(12) United States Patent
Ikeda et al.

(10) Patent No.: US 7,053,255 B2
(45) Date of Patent: May 30, 2006

(54) SUBSTITUTED DIPHENYLANTHRACENE COMPOUNDS FOR ORGANIC ELECTROLUMINESCENCE DEVICES

(75) Inventors: Hidetsugu Ikeda, Sodegaura (JP); Hiromasa Arai, Sodegaura (JP); Masakazu Funahashi, Sodegaura (JP); Chishio Hosokawa, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 09/985,353

(22) Filed: Nov. 2, 2001

(65) Prior Publication Data

US 2004/0214035 A1    Oct. 28, 2004

(30) Foreign Application Priority Data

Nov. 8, 2000    (JP) ............................. 2000-339938

(51) Int. Cl.
  *C07C 15/00*    (2006.01)
  *C09K 11/06*    (2006.01)
(52) U.S. Cl. ................... 585/26; 252/301.16; 313/504; 428/917
(58) Field of Classification Search ........... 252/301.16; 428/690, 917; 313/504, 506; 585/26
  See application file for complete search history.

(56) References Cited

U.S. PATENT DOCUMENTS

| | | | | |
|---|---|---|---|---|
| 4,769,292 A | * | 9/1988 | Tang et al. | 428/690 |
| 5,635,308 A | * | 6/1997 | Inoue et al. | 428/690 |
| 5,972,247 A | * | 10/1999 | Shi et al. | 252/583 |
| 6,730,419 B1 | * | 5/2004 | Kim et al. | 428/690 |
| 6,803,120 B1 | * | 10/2004 | Fukuoka et al. | 428/690 |
| 2002/0028346 A1 | * | 3/2002 | Shi et al. | 428/690 |

FOREIGN PATENT DOCUMENTS

| | | |
|---|---|---|
| EP | 1 009 041 A2 | 8/2000 |
| JP | 8-012969 | 1/1996 |
| JP | 11-323323 | 11/1999 |
| JP | 2000-007604 | 1/2000 |
| JP | 2000-53677 A * | 2/2000 |
| JP | 2000-143569 | 5/2000 |

OTHER PUBLICATIONS

Machine-assisted translation of JP 2000-007604 Jan. 2000.*
Machine-assisted translation of JP 2000-053677 Feb. 2000.*

* cited by examiner

*Primary Examiner*—Marie Yamnitzky
(74) *Attorney, Agent, or Firm*—Steptoe & Johnson LLP

(57) ABSTRACT

A compound having a of the present invention has the diphenylanthracene structure at the center and a specific structure substituted with an aryl group at end portions. An organic electroluminescence device comprises a plurality of layers of thin films of organic compounds which comprise a light emitting layer or a plurality of layers comprising a light emitting layer and are disposed between a pair of electrodes and at least one of the layers of thin films of organic compounds comprises the above compound. The compound exhibits excellent efficiency of light emission and heat resistance, has a long life and emits bluish light having excellent purity of color and the organic electroluminescence device comprises the compound and exhibits the same advantageous properties.

1 Claim, 1 Drawing Sheet

SUBSTITUTED DIPHENYLANTHRACENE COMPOUNDS FOR ORGANIC ELECTROLUMINESCENCE DEVICES

TECHNICAL FIELD

The present invention relates to a novel compound which is used as a light source such as a planar light emitting member of wall televisions and a back light of displays, exhibits excellent efficiency of light emission and heat resistance, has a long life and emits bluish light having excellent purity of color and to an organic electroluminescence device utilizing the novel compound.

BACKGROUND ART

Electroluminescence (referred to as EL, hereinafter) devices using organic substances are expected to be used for inexpensive full color display devices of the solid light emission type which can display a large area and development thereof has been actively conducted. In general, an EL device is constituted with a light emitting layer and a pair of electrodes faced to each other at both sides of the light emitting layer. When a voltage is applied between the electrodes, electrons are injected at the side of the cathode and holes are injected at the side of the anode. The electrons are combined with the holes in the light emitting layer and an excited state is formed. When the excited state returns to the ground state, the energy is emitted as light.

Organic EL devices used heretofore have higher driving voltages, lower luminances of emitted light and lower efficiencies of light emission than inorganic light emitting diodes and, moreover, the properties of organic EL devices deteriorate rather rapidly. Therefore, organic EL devices have not been used for practical applications. Although the properties of recent organic EL devices have been improved remarkably, the efficiency of light emission, the heat resistance and the life are not sufficient for practical applications.

For example, an organic EL device using a dimer or a trimer of phenylanthracene is disclosed in Japanese Patent Application Laid-Open No. Heisei 8(1996)-12600. However, since the above compound used in the device contains two or three anthracene structures bonded through a conjugated group, the organic EL device has a small energy gap and exhibits poor purity of color in emission of blue light. Moreover, since this compound is easily oxidized, impurities tend to be contained and a problem arises with respect to purification. To overcome the above problems, preparation of organic EL devices using a compound in which the 1-position and the 9-position of anthracene are substituted with naphthalene or a compound in which m-position of phenyl group in diphenylanthracene is substituted with an aryl group have been examined. However, the prepared organic EL devices exhibit low efficiencies of light emission and cannot be used for practical applications.

An organic EL device using a monoanthracene derivative substituted with naphthalene is disclosed in Japanese Patent Application Laid-Open No. Heisei 11(1999)-3782. However, this device exhibits an efficiency of light emission as low as 1 cd/a and cannot be used for practical applications. An organic EL device using a compound having a phenylanthracene structure is disclosed in U.S. Pat. No. 5,972,247. However, this device exhibits an efficiency of light emission as low as 2 cd/A and cannot be used for practical applications although the device exhibits excellent heat resistance due to the substitution with an aryl group at the m-position.

DISCLOSURE OF THE INVENTION

The present invention has been made to overcome the above problems and has an object of providing a novel compound which exhibits excellent efficiency of light emission and heat resistance, has a long life and emits bluish light having excellent purity of color and an organic electroluminescence device utilizing the novel compound.

As the result of extensive studies by the present inventors to develop a novel compound having above advantageous properties and an organic EL device using the novel compound, it was found that the object can be achieved by using a compound having the diphenylanthracene structure at the center and a specific structure substituted with an aryl group at end portions. The present invention has been completed based on the knowledge.

The novel compound of the present invention comprises compounds represented by the following general formulae [1], [1'] and [2] to [5].

General formula [1]:

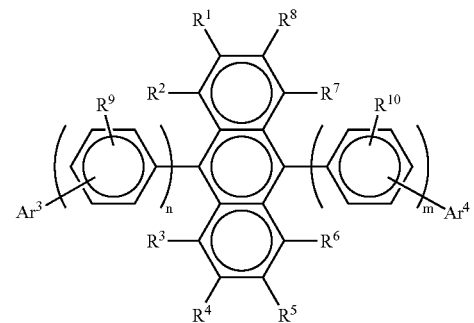

wherein $R^1$ to $R^{10}$ each independently represent hydrogen atom, a halogen atom, cyano group, nitro group, a substituted or unsubstituted alkyl group having 1 to 20 carbon atoms, a substituted or unsubstituted alkoxyl group having 1 to 20 carbon atoms, a substituted or unsubstituted aryloxyl group having 6 to 30 carbon atoms, a substituted or unsubstituted alkylthio group having 1 to 20 carbon atoms, a substituted or unsubstituted arylthio group having 6 to 30 carbon atoms, a substituted or unsubstituted arylalkyl group having 7 to 30 carbon atoms, an unsubstituted monocyclic group having 5 to 30 carbon atoms, a substituted or unsubstituted condensed polycyclic group having 10 to 30 carbon atoms or a substituted or unsubstituted heterocyclic group having 5 to 30 carbon atoms;

$Ar^3$ and $Ar^4$ each independently represent a substituted or unsubstituted aryl group having 6 to 30 carbon atoms or a substituted or unsubstituted alkenyl group having 2 to 10 carbon atoms, the substituent in the above groups being a substituted or unsubstituted alkyl group having 1 to 20 carbon atoms, a substituted or unsubstituted alkoxyl group having 1 to 20 carbon atoms, a substituted or unsubstituted aryloxyl group having 6 to 30 carbon atoms, a substituted or unsubstituted alkylthio group having 1 to 20 carbon atoms, a substituted or unsubstituted arylthio group having 6 to 30 carbon atoms, a substituted or unsubstituted arylalkyl group having 7 to 30 carbon atoms, an unsubstituted monocyclic group having 5 to 30 carbon atoms, a substituted or unsubstituted condensed polycyclic group having 10 to 30 carbon atoms, a substituted or unsubstituted heterocyclic group having 5 to 30 carbon atoms or a substituted or unsubstituted alkenyl group having 4 to 40 carbon atoms;

n represents a number of 1 to 3 and m represents a number of 1 to 3; and a case in which $Ar^3$ and $Ar^4$ both represent an alkenyl group and n and m both represent a number of 1 is excluded.

General formula [1']:

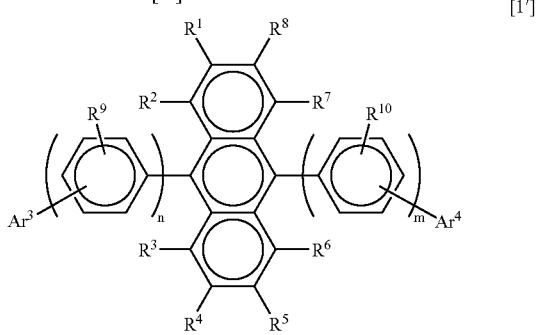

[1']

wherein $R^1$ to $R^{10}$ each independently represent hydrogen atom, a halogen atom, cyano group, nitro group, a substituted or unsubstituted alkyl group having 1 to 20 carbon atoms, a substituted or unsubstituted alkoxyl group having 1 to 20 carbon atoms, a substituted or unsubstituted aryloxyl group having 6 to 30 carbon atoms, a substituted or unsubstituted alkylthio group having 1 to 20 carbon atoms, a substituted or unsubstituted arylthio group having 6 to 30 carbon atoms, a substituted or unsubstituted arylalkyl group having 7 to 30 carbon atoms, an unsubstituted monocyclic group having 5 to 30 carbon atoms, a substituted or unsubstituted condensed polycyclic group having 10 to 30 carbon atoms or a substituted or unsubstituted heterocyclic group having 5 to 30 carbon atoms;

$Ar^3$ and $Ar^4$ each independently represent a substituted or unsubstituted aryl group having 6 to 30 carbon atoms or a substituted or unsubstituted alkenyl group having 2 to 10 carbon atoms, the substituent in the above groups being a substituted or unsubstituted alkyl group having 1 to 20 carbon atoms, a substituted or unsubstituted alkoxyl group having 1 to 20 carbon atoms, a substituted or unsubstituted aryloxyl group having 6 to 30 carbon atoms, a substituted or unsubstituted alkylthio group having 1 to 20 carbon atoms, a substituted or unsubstituted arylthio group having 6 to 30 carbon atoms, a substituted or unsubstituted arylalkyl group having 7 to 30 carbon atoms, an unsubstituted monocyclic group having 5 to 30 carbon atoms, a substituted or unsubstituted condensed polycyclic group having 10 to 30 carbon atoms, a substituted or unsubstituted heterocyclic group having 5 to 30 carbon atoms or a substituted or unsubstituted alkenyl group having 4 to 40 carbon atoms; and n represents a number of 1 to 3, m represents a number of 1 to 3 and a case in which n and m represent a same number is excluded.

General formula [2]:

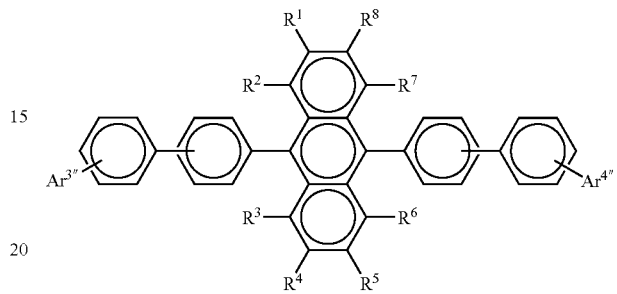

[2]

wherein $R^1$ to $R^8$ each independently represent hydrogen atom, a halogen atom, cyano group, nitro group, a substituted or unsubstituted alkyl group having 1 to 20 carbon atoms, a substituted or unsubstituted alkoxyl group having 1 to 20 carbon atoms, a substituted or unsubstituted aryloxyl group having 6 to 30 carbon atoms, a substituted or unsubstituted alkylthio group having 1 to 20 carbon atoms, a substituted or unsubstituted arylthio group having 6 to 30 carbon atoms, a substituted or unsubstituted arylalkyl group having 7 to 30 carbon atoms, an unsubstituted monocyclic group having 5 to 30 carbon atoms, a substituted or unsubstituted condensed polycyclic group having 10 to 30 carbon atoms or a substituted or unsubstituted heterocyclic group having 5 to 30 carbon atoms; and $Ar^{3\prime\prime}$ and $Ar^{4\prime\prime}$ each independently represent a substituted or unsubstituted aryl group having 6 to 30 carbon atoms, the substituent in the above group being a substituted or unsubstituted alkyl group having 1 to 20 carbon atoms, a substituted or unsubstituted alkoxyl group having 1 to 20 carbon atoms, a substituted or unsubstituted aryloxyl group having 6 to 30 carbon atoms, a substituted or unsubstituted alkylthio group having 1 to 20 carbon atoms, a substituted or unsubstituted arylthio group having 6 to 30 carbon atoms, a substituted or unsubstituted arylalkyl group having 6 to 30 carbon atoms, an unsubstituted monocyclic group having 5 to 30 carbon atoms, a substituted or unsubstituted condensed polycyclic group having 10 to 30 carbon atoms, a substituted or unsubstituted heterocyclic group having 5 to 30 carbon atoms or a substituted or unsubstituted alkenyl group having 4 to 40 carbon atoms.

General formula [3]:

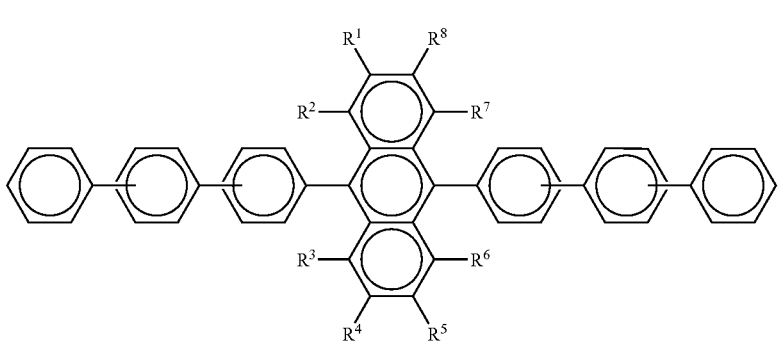

[3]

wherein $R^1$ to $R^8$ each independently represent hydrogen atom, a halogen atom, cyano group, nitro group, a substituted or unsubstituted alkyl group having 1 to 20 carbon atoms, a substituted or unsubstituted alkoxyl group having 1 to 20 carbon atoms, a substituted or unsubstituted aryloxyl group having 6 to 30 carbon atoms, a substituted or unsubstituted alkylthio group having 1 to 20 carbon atoms, a substituted or unsubstituted arylthio group having 6 to 30 carbon atoms, a substituted or w unsubstituted arylalkyl group having 7 to 30 carbon atoms, an unsubstituted monocyclic group having 5 to 30 carbon atoms, a substituted or unsubstituted condensed polycyclic group having 10 to 30 carbon atoms or a substituted or unsubstituted heterocyclic group having 5 to 30 carbon atoms.

General formula [4]:

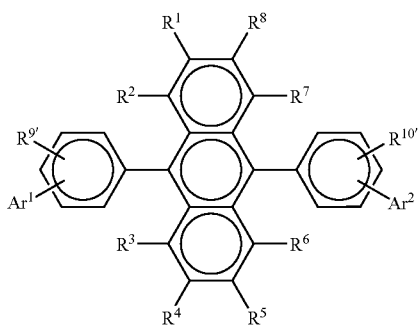

[4]

wherein $R^1$ to $R^8$ each independently represent hydrogen atom, a halogen atom, cyano group, nitro group, a substituted or unsubstituted alkyl group having 1 to 20 carbon atoms, a substituted or unsubstituted alkoxyl group having 1 to 20 carbon atoms, a substituted or unsubstituted aryloxyl group having 6 to 30 carbon atoms, a substituted or unsubstituted alkylthio group having 1 to 20 carbon atoms, a substituted or unsubstituted arylthio group having 6 to 30 carbon atoms, a substituted or unsubstituted arylalkyl group having 7 to 30 carbon atoms, an unsubstituted monocyclic group having 5 to 30 carbon atoms, a substituted or unsubstituted condensed polycyclic group having 10 to 30 carbon atoms or a substituted or unsubstituted heterocyclic group having 5 to 30 carbon atoms;

$R^{9'}$ and $R^{10'}$ each independently represent a substituted or unsubstituted alkenyl group having 8 to 30 carbon atoms; and $Ar^1$ and $Ar^1$ each independently represent and a substituted or unsubstituted aryl group having 6 to 30 carbon atoms, the substituent in the above group being a substituted or unsubstituted alkyl group having 1 to 20 carbon atoms, a substituted or unsubstituted alkoxyl group having 1 to 20 carbon atoms, a substituted or unsubstituted aryloxyl group having 6 to 30 carbon atoms, a substituted or unsubstituted alkylthio group having 1 to 20 carbon atoms, a substituted or unsubstituted arylthio group having 6 to 30 carbon atoms, a substituted or unsubstituted arylalkyl group having 7 to 30 carbon atoms, an unsubstituted monocyclic group having 5 to 30 carbon atoms, a substituted or unsubstituted condensed polycyclic group having 10 to 30 carbon atoms or a substituted or unsubstituted heterocyclic group having 5 to 30 carbon atoms.

General formula [5]:

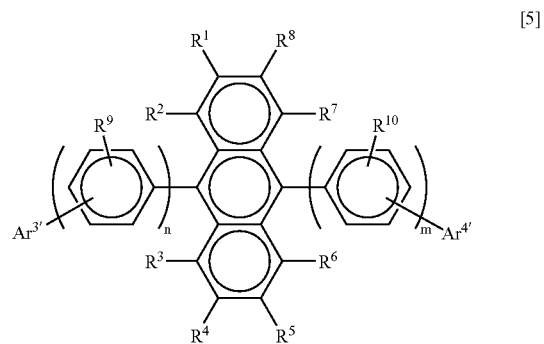

[5]

wherein $R^1$ to $R^{10}$ each independently represent hydrogen atom, a halogen atom, cyano group, nitro group, a substituted or unsubstituted alkyl group having 1 to 20 carbon atoms, a substituted or unsubstituted alkoxyl group having 1 to 20 carbon atoms, a substituted or unsubstituted aryloxyl group having 6 to 30 carbon atoms, a substituted or unsubstituted alkylthio group having 1 to 20 carbon atoms, a substituted or unsubstituted arylthio group having 6 to 30 carbon atoms, a substituted or unsubstituted arylalkyl group having 7 to 30 carbon atoms, an unsubstituted monocyclic group having 5 to 30 carbon atoms, a substituted or unsubstituted condensed polycyclic group having 10 to 30 carbon atoms or a substituted or unsubstituted heterocyclic group having 5 to 30 carbon atoms, and at least one of $R^1$ to $R^8$ represents the alkyl group, the alkoxyl group, the aryloxyl group, the alkylthio group, the arylthio group, the arylalkyl group, the monocyclic group, the condensed polycyclic group or the heterocyclic group;

$Ar^{3'}$ and $Ar^{4'}$ each independently represent a substituted or unsubstituted alkenyl group having 8 to 30 carbon atoms; and n represents a number of 1 or 2 and m represents a number of 1 or 2.

The organic EL device of the present invention comprises a plurality of layers of thin films of organic compounds which comprise a light emitting layer or a plurality of layers comprising a light emitting layer and are disposed between a pair of electrodes, wherein at least one of the layers of thin films of organic compounds comprises any of novel compounds represented by general formulae [1], [1'] and [2] to [5].

It is preferable that the light emitting layer comprises any of novel compounds represented by general formulae [1], [1'] and [2] to [5].

The light emitting layer may comprise any of novel compounds represented by general formulae [1], [1'] and [2] to [5] and a fluorescent dopant.

It is preferable that the organic EL device emits light having a peak wavelength of 460 nm or shorter.

It is preferable that the fluorescent dopant is an amine compound.

THE MOST PREFERRED EMBODIMENT TO CARRY OUT THE INVENTION

Figure 1:
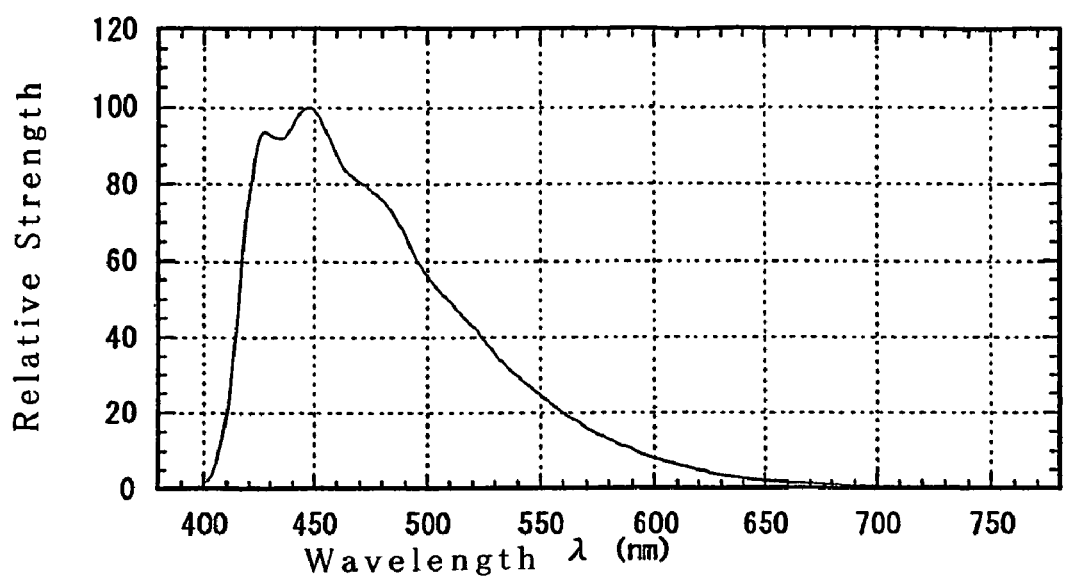
FIG. 1 shows a spectrum of the organic EL device of Example 1 of the present invention.

The novel compound of the present invention useful for the organic EL device which emits bluish light is represented by one of the above formulae [1], [1'] and [2] to [5].

$R^1$ to $R^{10}$ in the above general formulae [1] and [1'] each independently represent hydrogen atom, a halogen atom, cyano group, nitro group, a substituted or unsubstituted alkyl group having 1 to 20 carbon atoms, a substituted or unsubstituted alkoxyl group having 1 to 20 carbon atoms, a substituted or unsubstituted aryloxyl group having 6 to 30 carbon atoms, a substituted or unsubstituted alkylthio group having 1 to 20 carbon atoms, a substituted or unsubstituted arylthio group having 6 to 30 carbon atoms, a substituted or unsubstituted arylalkyl group having 7 to 30 carbon atoms, an unsubstituted monocyclic group having 5 to 30 carbon atoms, a substituted or unsubstituted condensed polycyclic group having 10 to 30 carbon atoms or a substituted or unsubstituted heterocyclic group having 5 to 30 carbon atoms.

$Ar^3$ and $Ar^4$ in the in the above general formulae [1] and [1'] each independently represent a substituted or unsubstituted aryl group having 6 to 30 carbon atoms or a substituted or unsubstituted alkenyl group having 2 to 10 carbon atoms The substituent to the above groups is a substituted or unsubstituted alkyl group having 1 to 20 carbon atoms, a substituted or unsubstituted alkoxyl group having 1 to 20 carbon atoms, a substituted or unsubstituted aryloxyl group having 6 to 30 carbon atoms, a substituted or unsubstituted alkylthio group having 1 to 20 carbon atoms, a substituted or unsubstituted arylthio group having 6 to 30 carbon atoms, a substituted or unsubstituted arylalkyl group having 7 to 30 carbon atoms, an unsubstituted monocyclic group having 5 to 30 carbon atoms, a substituted or unsubstituted condensed polycyclic group having 10 to 30 carbon atoms, a substituted or unsubstituted heterocyclic group having 5 to 30 carbon atoms or a substituted or unsubstituted alkenyl group having 4 to 40 carbon atoms.

In the above general formulae [1] and [1'], n represents a number of 1 to 3 and m represents a number of 1 to 3. However, the case in which $Ar^3$ and $Ar^4$ both represent an alkenyl group and n and m both represent a number of 1 is excluded in general formula [1] and the case in which n and m represent the same number is excluded in general formula [1'].

In the above general formula [2], $R^1$ to $R^8$ are the same as $R^1$ to $R^8$ defined in general formula [1].

In the above general formula [2], $Ar^{3''}$ and $Ar^{4''}$ each independently represent a substituted or unsubstituted aryl group having 6 to 30. The substituent in the above group is a substituted or unsubstituted alkyl group having 1 to 20 carbon atoms, a substituted or unsubstituted alkoxyl group having 1 to 20 carbon atoms, a substituted or unsubstituted aryloxyl group having 6 to 30 carbon atoms, a substituted or unsubstituted alkylthio group having 1 to 20 carbon atoms, a substituted or unsubstituted arylthio group having 6 to 30 carbon atoms, a substituted or unsubstituted arylalkyl group having 6 to 30 carbon atoms, an unsubstituted monocyclic group having 5 to 30 carbon atoms, a substituted or unsubstituted condensed polycyclic group having 10 to 30 carbon atoms, a substituted or unsubstituted heterocyclic group having 5 to 30 carbon atoms or a substituted or unsubstituted alkenyl group having 4 to 40 carbon atoms.

In the above general formula [3], $R^1$ to $R^8$ are the same as $R^1$ to $R^8$ defined in general formula [1].

In the above general formula [4], $R^1$ to $R^8$ are the same as $R^1$ to $R^8$ defined in general formula [1] and $R^{9'}$ and $R^{10'}$ each independently represent a substituted or unsubstituted alkenyl group having 8 to 30 carbon atoms.

In the above general formula [4], $Ar^1$ and $Ar^1$ each independently represent a substituted or unsubstituted aryl group having 6 to 30 carbon atoms. The substituent to the above group is a substituted or unsubstituted alkyl group having 1 to 20 carbon atoms, a substituted or unsubstituted alkoxyl group having 1 to 20 carbon atoms, a substituted or unsubstituted aryloxyl group having 6 to 30 carbon atoms, a substituted or unsubstituted alkylthio group having 1 to 20 carbon atoms, a substituted or unsubstituted arylthio group having 6 to 30 carbon atoms, a substituted or unsubstituted arylalkyl group having 7 to 30 carbon atoms, an unsubstituted monocyclic group having 5 to 30 carbon atoms, a substituted or unsubstituted condensed polycyclic group having 10 to 30 carbon atoms or a substituted or unsubstituted heterocyclic group having 5 to 30 carbon atoms.

Since the groups represented by $R^{9'}$ and $R^{10'}$ in the compound represented by general formula [4] are alkenyl groups, the organic EL compound obtained by using this compound exhibits an enhanced fluorescent property and an improved efficiency of light emission.

In the above general formula [5], $R^1$ to $R^{10}$ are the same as $R^1$ to $R^{10}$ defined in general formula [1] with a proviso that at least one of $R^1$ to $R^8$ represents the alkyl group, the alkoxyl group, the aryloxyl group, the alkylthio group, the arylthio group, the arylalkyl group, the monocyclic group, the condensed polycyclic group or the heterocyclic group.

In the above general formula [5], $Ar^{3'}$ and $Ar^{4'}$ each independently represent a substituted or unsubstituted alkenyl group having 8 to 30 carbon atoms.

Since at least one of $R^1$ to $R^8$ represents the alkyl group, the alkoxyl group, the aryloxyl group, the alkylthio group, the arylthio group, the arylalkyl group, the monocyclic group, the condensed polycyclic group or the heterocyclic group in the above general formula [5], the organic EL compound obtained by using the compound represented by general formula [5] exhibits improved uniformity of light emission on the light emitting surface and the possibility of forming defects decreases.

Examples of the groups represented by $Ar^1$ to $Ar^4$ include the following groups:

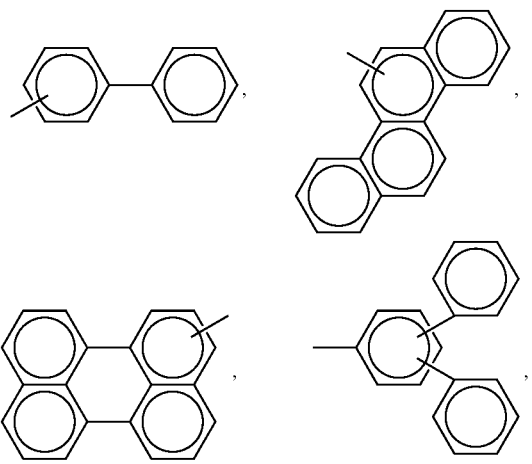

-continued

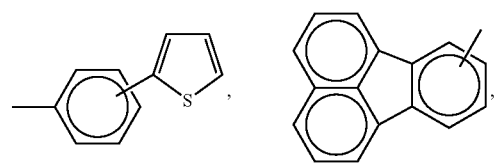
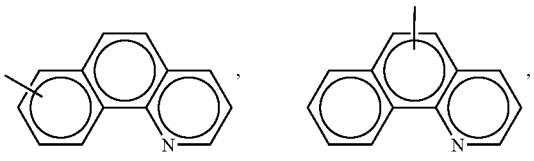
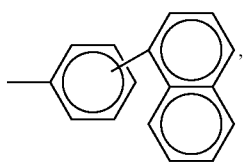
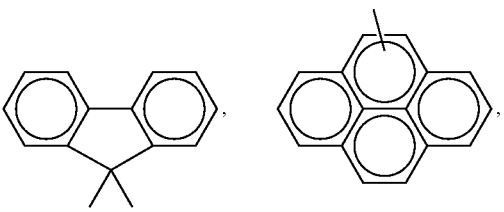
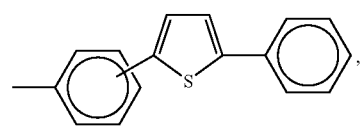
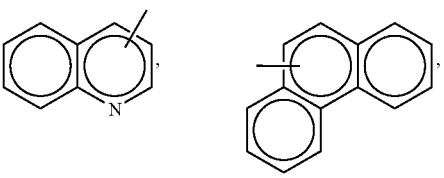
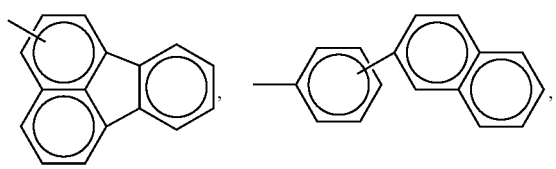
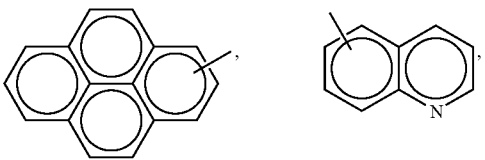
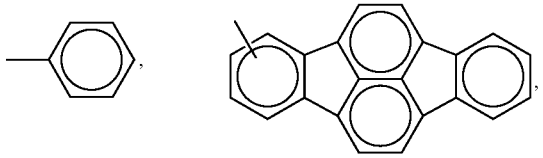
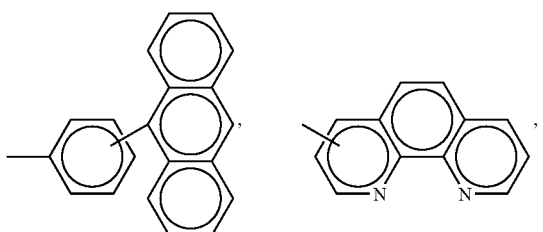
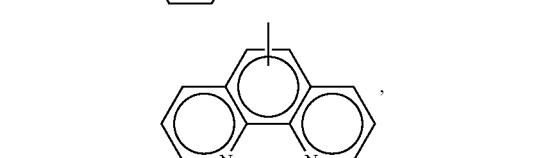
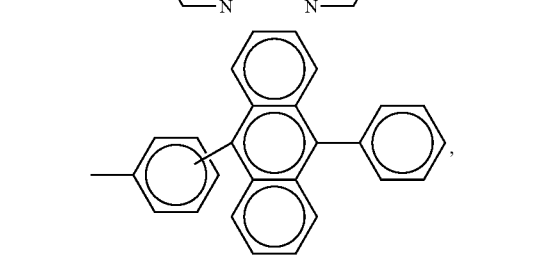

and the above groups having alkyl groups, alkoxyl groups or aryl groups as the substituents.

As described above, the organic EL device of the present invention comprises a plurality of layers of thin films of organic compounds which comprise a light emitting layer or a plurality of layers comprising a light emitting layer and are disposed between a pair of electrodes and at least one of the layers of thin films of organic compounds comprises any of the novel compounds represented by the above general formulae [1], [1'] and [2] to [5].

It is preferable that the layer of the thin films of organic compounds comprises 1 to 100% by mole and more preferably 10 to 98% by mole of any of the novel compounds represented by the above general formulae [1], [1'] and [2] to [5].

The organic EL device of the present invention emits bluish light.

Typical examples of the compounds represented by the above general formulae [1], [1'] and [2] to [5] are shown in the following as compounds (1) to (43). However, the novel compound of the present invention is not limited to the compounds shown as the examples.

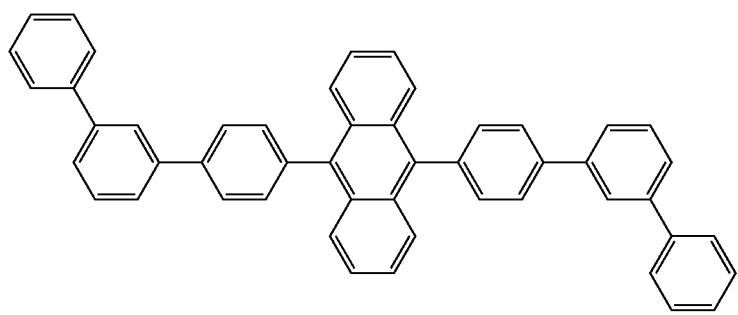
(1)
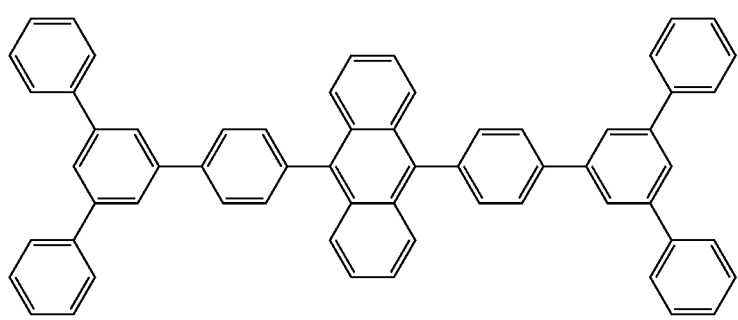
(2)
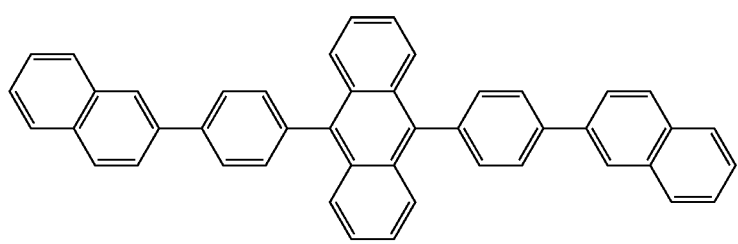
(3)
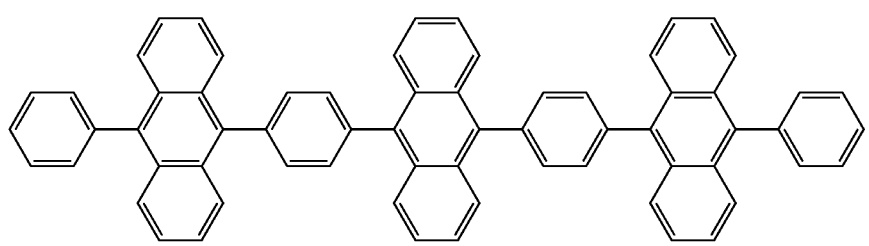
(4)
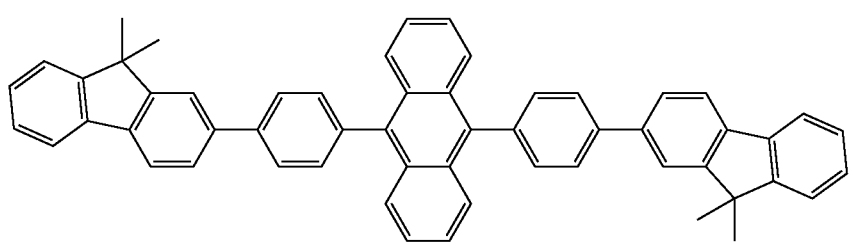
(5)
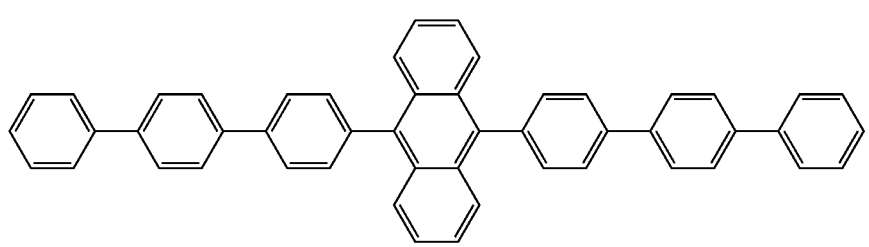
(6)

-continued
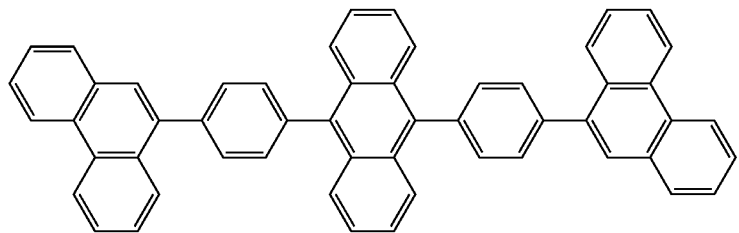
(7)
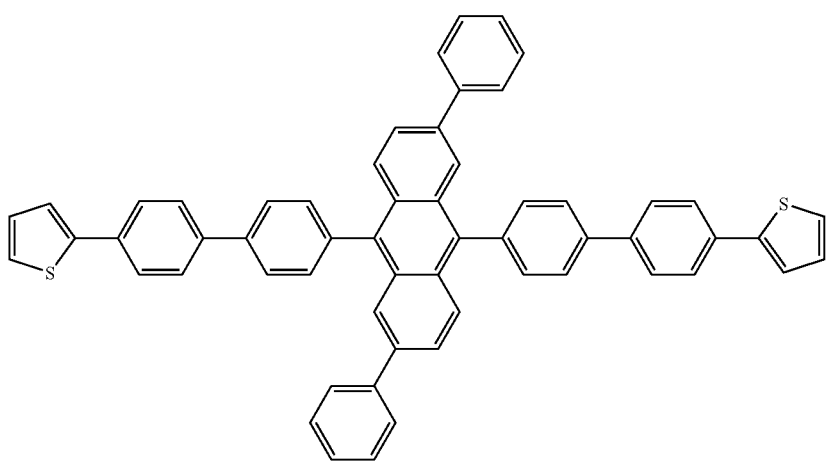
(8)
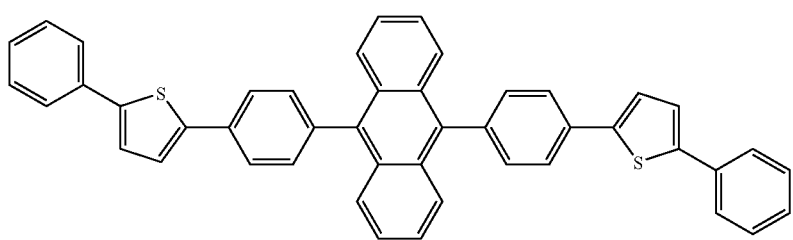
(9)
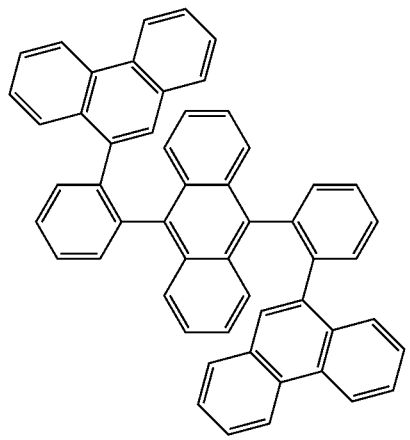
(10)

-continued
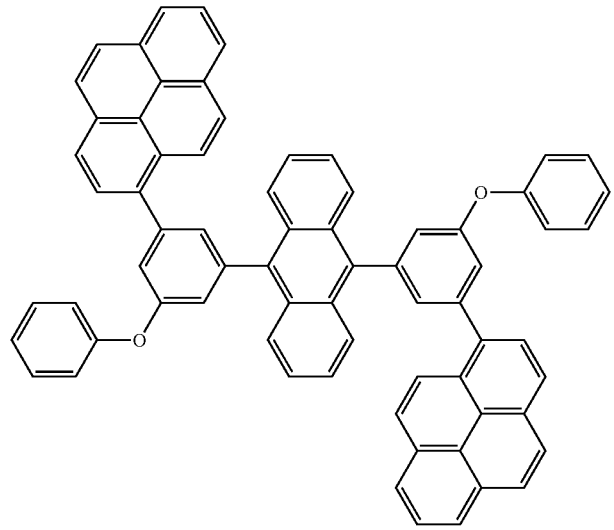
(11)
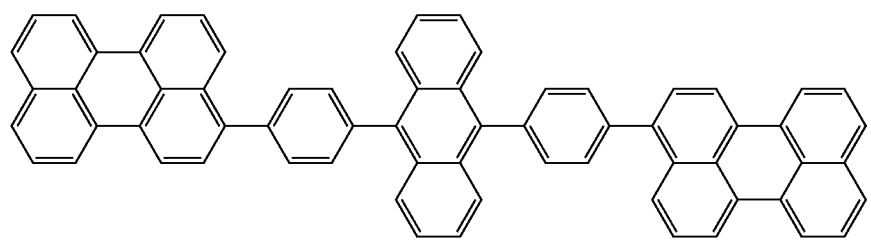
(12)
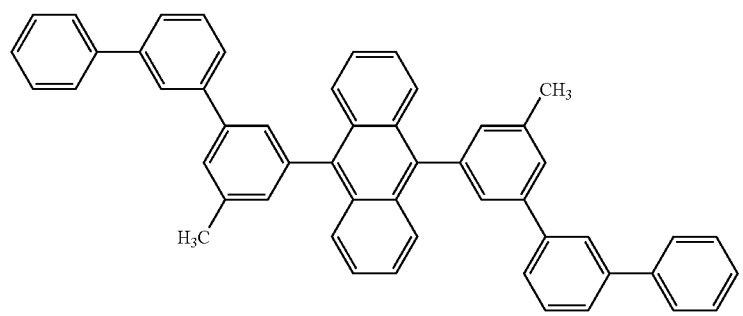
(13)
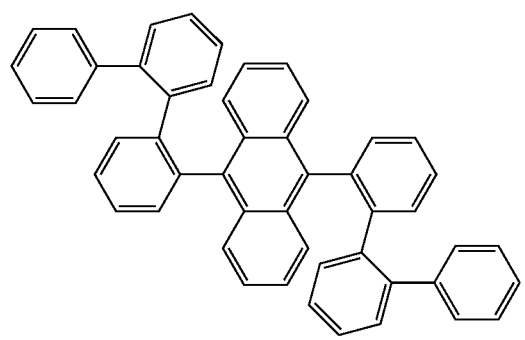
(14)

-continued
(15)
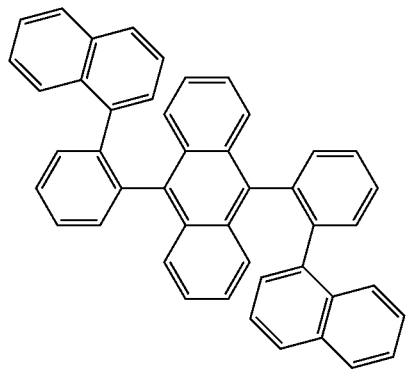
(16)
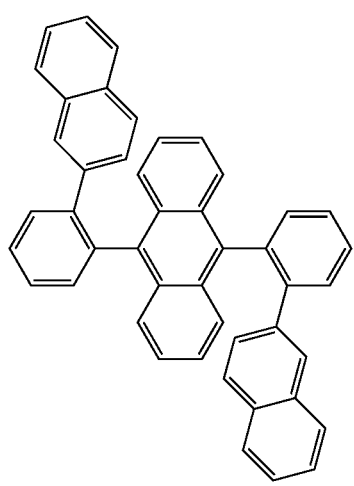
(17)
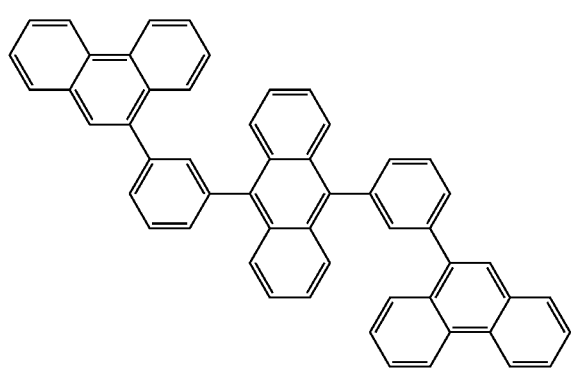
(18)
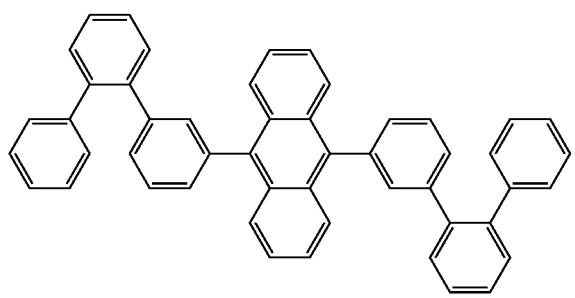

(19)
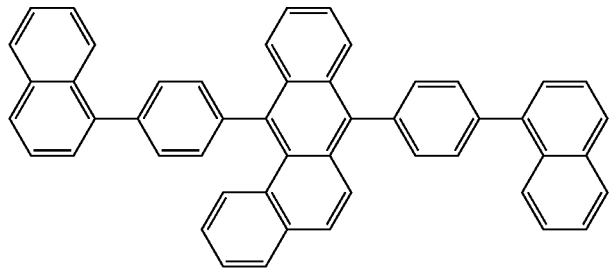
(20)
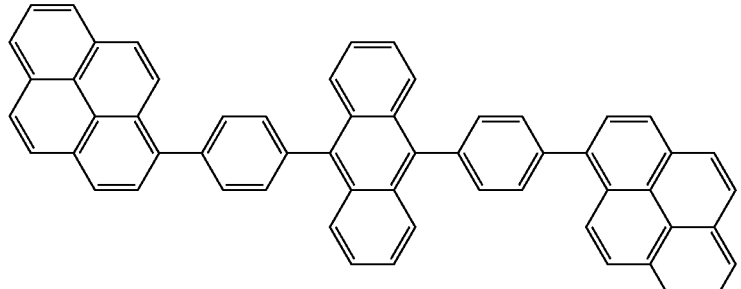
(21)
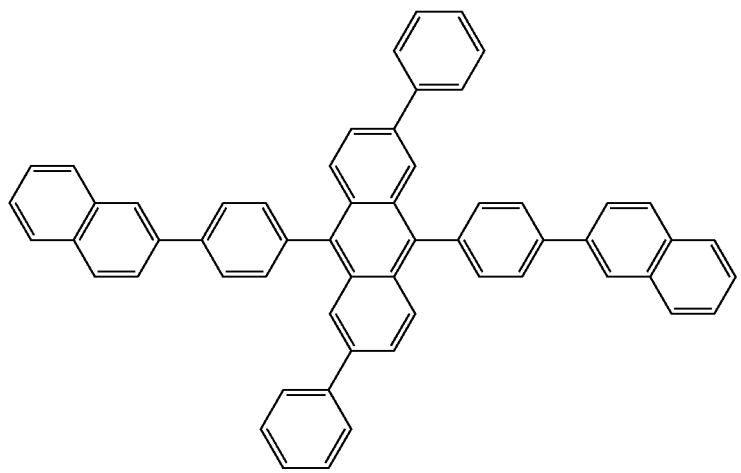
(22)
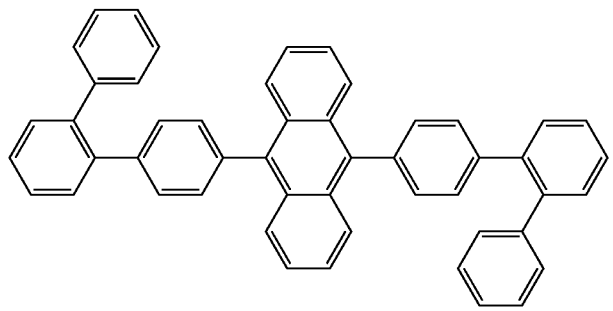
(23)
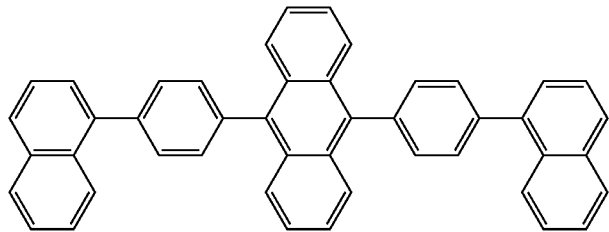

-continued
(24)
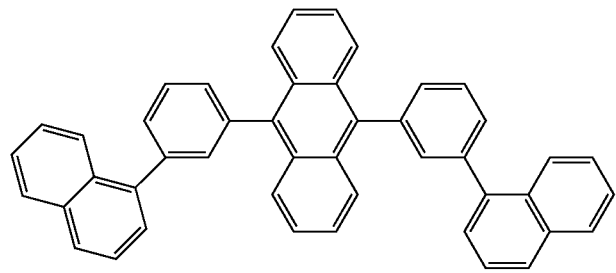
(25)
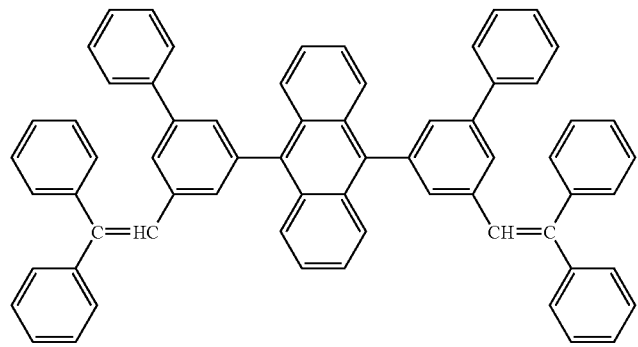
(26)
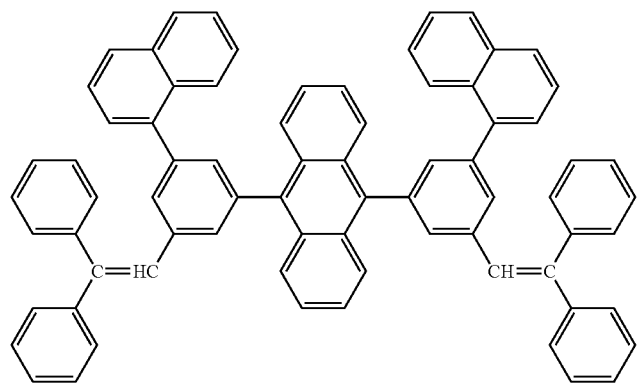
(27)
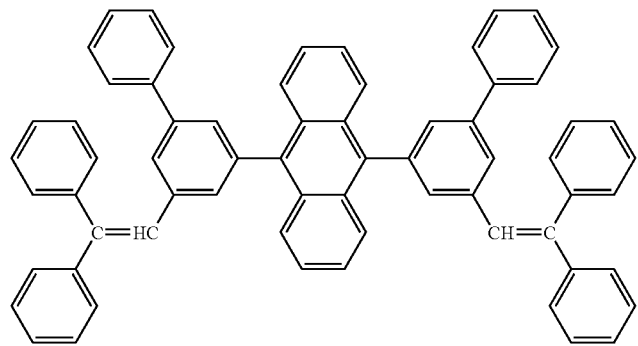
(28)
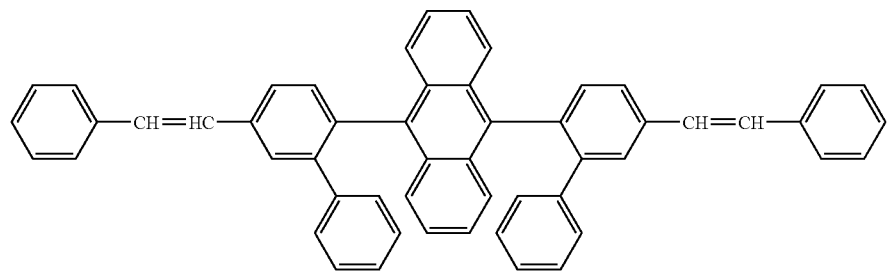

-continued
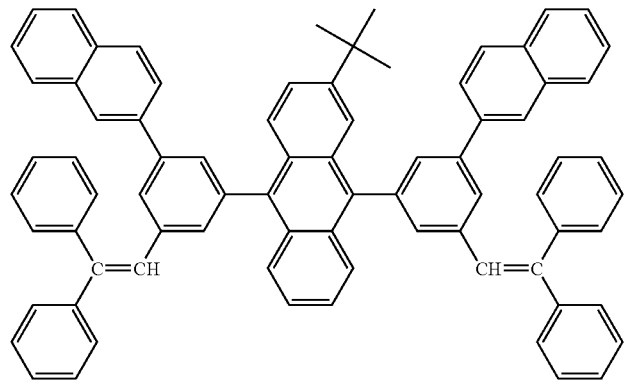
(29)
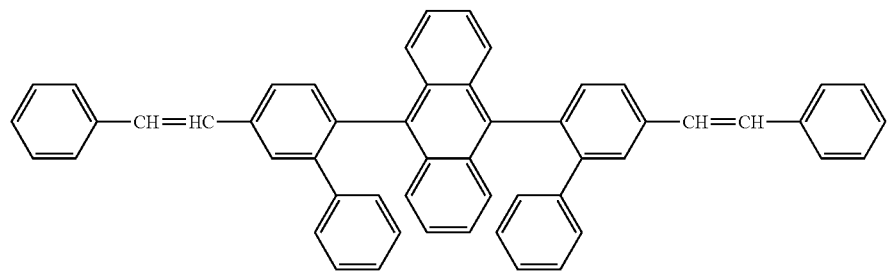
(30)
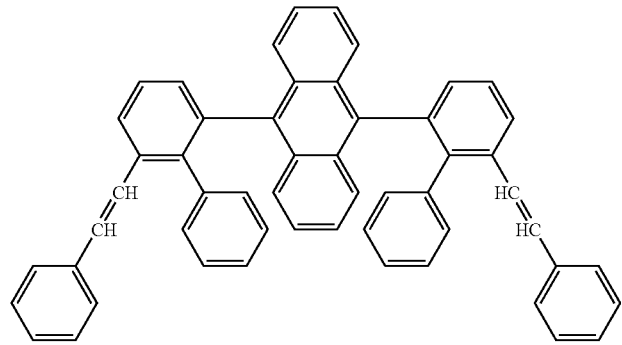
(31)
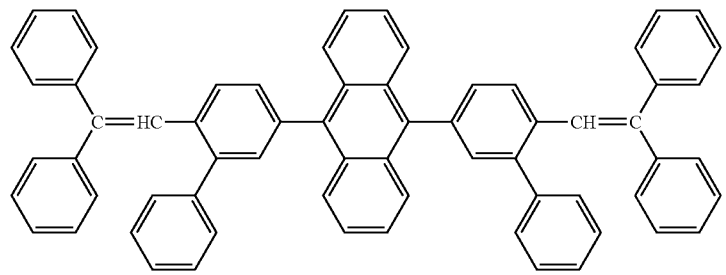
(32)
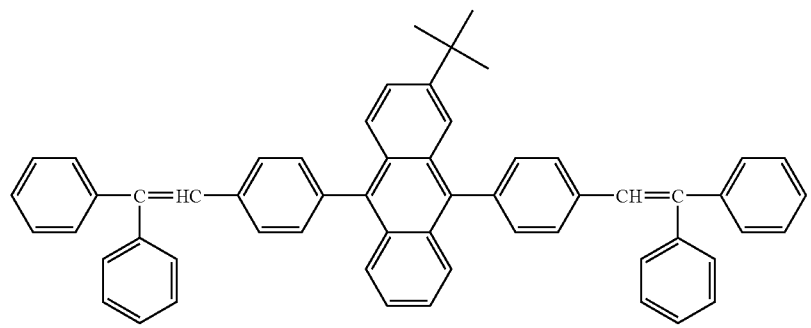
(33)

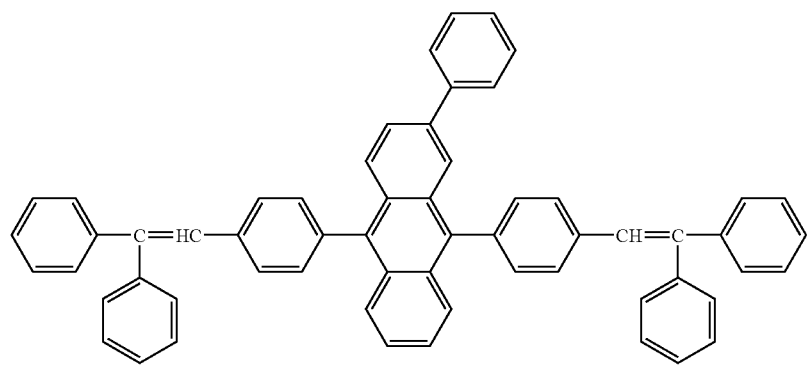
(34)
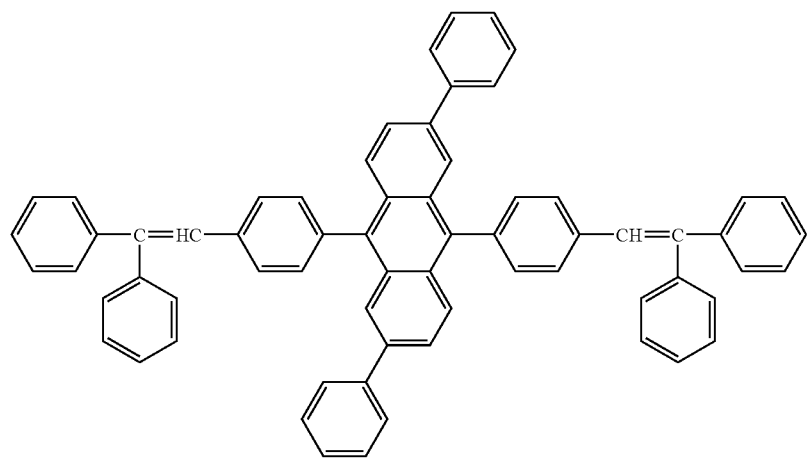
(35)
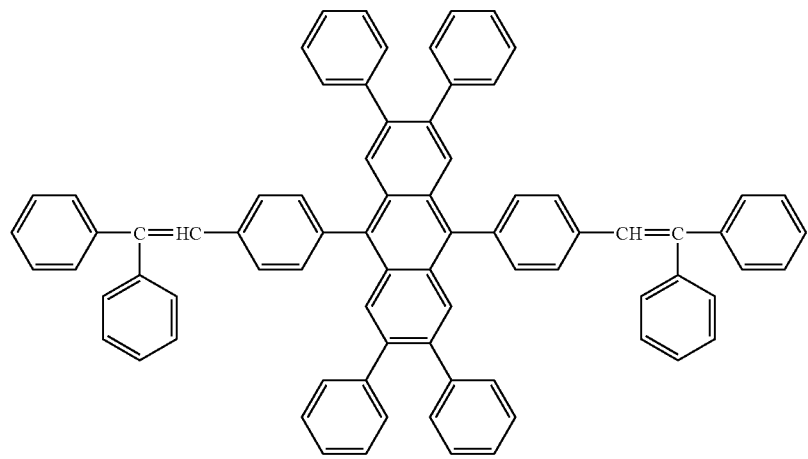
(36)
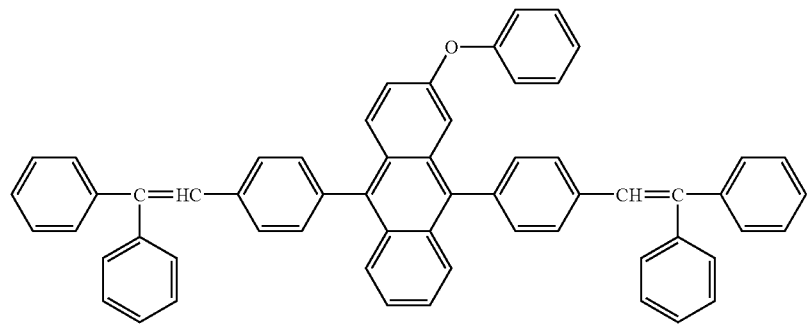
(37)

-continued
(38)
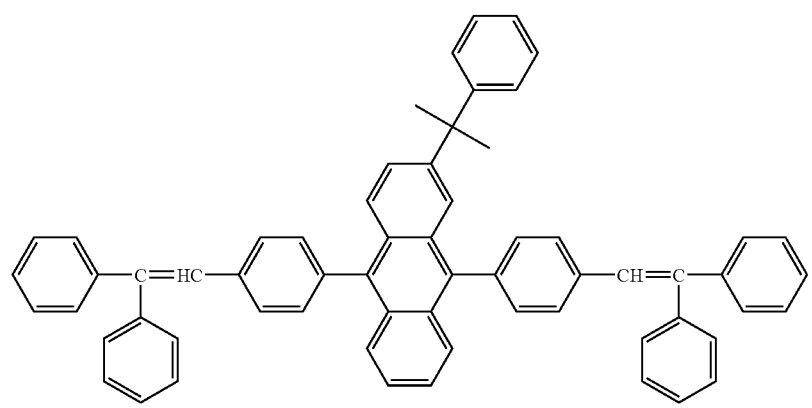
(39)
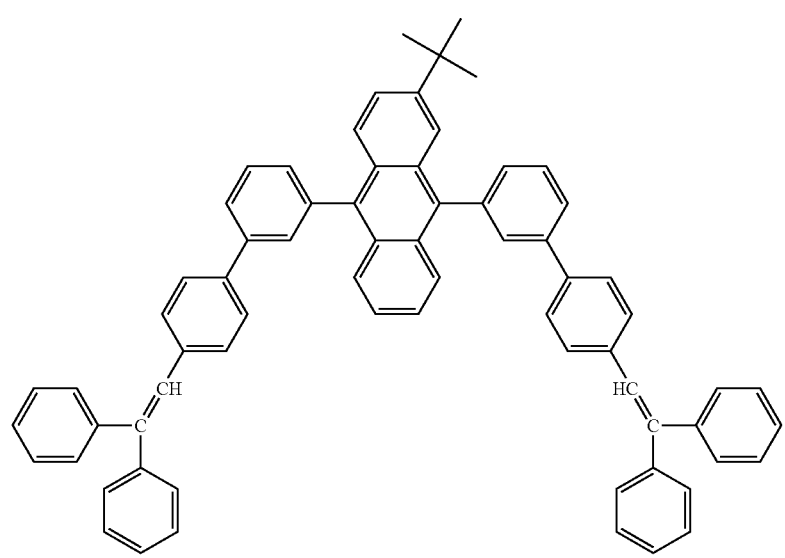
(40)
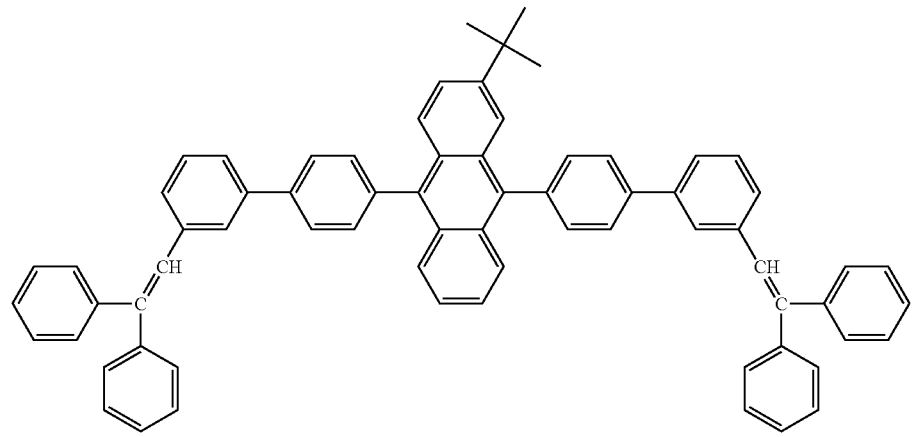

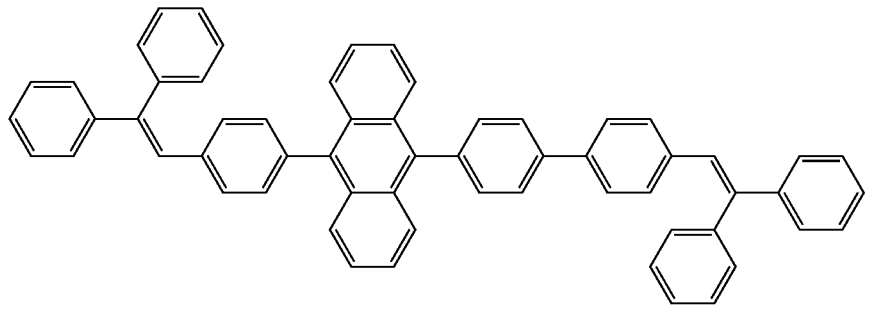

(41)

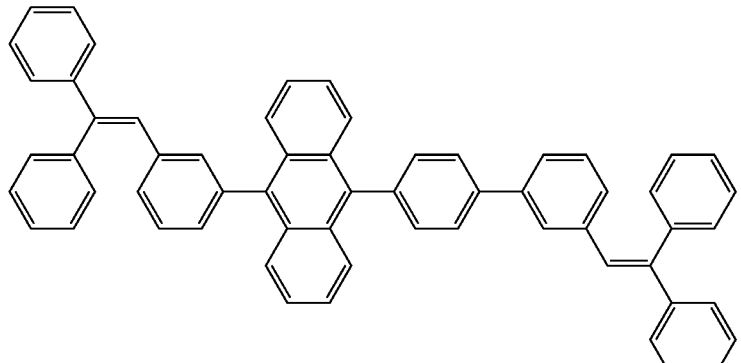

(42)

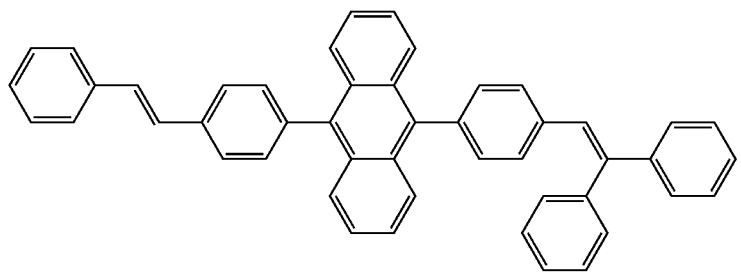

(43)

The organic EL device of the present invention is a device in which one or a plurality of organic thin films are disposed between an anode and a cathode. When the device has a single organic layer, a light emitting layer is disposed between an anode and a cathode. The light emitting layer contains a light emitting material and may also contain a hole injecting material to transport holes injected at the anode to the light emitting material or an electron injecting material to transport electrons injected at the cathode to the light emitting material. It is preferable that the light emitting layer is formed with a light emitting material having a very high quantum efficiency of fluorescence emission and excellent ability to transfer holes and electrons and a uniform thin film is formed. The organic EL device having a multi-layer structure has a laminate structure such as: (an anode/a hole injecting layer/a light emitting layer/a cathode), (an anode/a light emitting layer/an electron injecting layer/a cathode) and (an anode/a hole injecting layer/a light emitting layer/an electron injecting layer/a cathode).

In the light emitting layer, where necessary, conventional light emitting materials, doping materials, hole injecting materials and electron injecting materials may be used in addition to any of the compounds represented by general formulae [1], [1'] and [2] to [5] used in the present invention. Deterioration in the luminance and the life caused by quenching can be prevented by the multi-layer structure of the organic EL. Where necessary, light emitting materials, other doping materials, hole injecting materials and electron injecting materials may be used in combination. By using other doping materials, the luminance and the efficiency of light emission can be improved and red light and white light can be emitted. The hole injecting layer, the light emitting layer and the electron injecting layer may each have a multi-layer structure having two or more layers. When the hole injecting layer has a multi-layer structure, the layer into which holes are injected from the electrode is referred to as the hole injecting layer and the layer which receives holes from the hole injecting layer and transports holes from the hole injecting layer to the light emitting layer is referred to as the hole transporting layer. When the electron injecting layer has a multi-layer structure, the layer into which electrons are injected from the electrode is referred to as the electron injecting layer and the layer which receives electrons from the electron injecting layer and transports electrons from the electron injecting layer to the light emitting layer is referred to as the electron transporting layer. These layers are each selected and used in accordance with factors such as the energy level, heat resistance and adhesion with the organic layers or the metal electrodes of the material.

Examples of the material which can be used in the organic layer as the light emitting material or the host material in combination with any of the compounds represented by general formulae [1], [1'] and [2] to [5] include anthracene, naphthalene, phenanthrene, pyrene, tetracene, coronene, chrysene, fluoresceine, perylene, phthaloperylene, naphthaloperylene, perynone, phthaloperynone, naphthaloperynone, diphenylbutadiene, tetraphenylbutadiene, coumarine, oxadiazole, aldazine, bisbenzoxazoline, bisstyryl, pyrazine, cyclopentadiene, metal complexes of quinoline, metal complexes of aminoquinoline, metal complexes of benzoquinoline, imines, diphenylethylene, vinylanthracene, diaminocarbazole, pyrane, thiopyrane, polymethine, merocyanine, chelates of oxinoid compounds with imidazoles, quinacridone, rubrene, stilbene derivatives and fluorescent pigments. However, the above material is not limited to the compounds described above as the examples.

As the hole injecting material, a compound which has the ability to transfer holes, exhibits an excellent effect of hole injection from the anode and an excellent effect of hole injection to the light emitting layer or the light emitting material, prevents transfer of excited components formed in the light emitting layer into the electron injecting layer or the electron injecting material and has excellent ability to form a thin film is preferable. Examples of the above compound include phthalocyanine derivatives, naphthalocyanine derivatives, porphyrin derivatives, oxazole, oxadiazole, triazole, imidazole, imidazolone, imdazolethione, pyrazoline, pyrazolone, tetrahydroimidazole, oxazole, oxadiazole, hydrazone, acylhydrazone, polyarylalkanes, stilbene, butadiene, triphenylamines of the benzidine-type, triphenylamines of the styrylamine type, triphenylamines of the diamine type, derivatives of these compounds and macromolecular compounds such as polyvinylcarbazole, polysilane and conductive macromolecules. However, the above compound is not limited to the compounds described above as the examples.

Among the hole injection materials which can be used in the organic EL device of the present invention, aromatic tertiary amine derivatives and phthalocyanine derivatives are more effective.

Examples of the aromatic tertiary amine derivative include triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N', N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl) phenanthrene-9,10-diamine, N,N-bis(4-di-4-tolylaminophenyl)-4-phenylcyclohexane and oligomers and polymers having a skeleton structure of these aromatic tertiary amines. However, the aromatic tertiary amine derivative is not limited to the compounds described above as the examples.

Examples of the phthalocyanine (Pc) derivative include H$_2$Pc, CuPc, CoPc, NiPc, ZnPc, PdPc, FePc, MnPc, ClAlPc, ClGaPc, ClInPc, ClSnPc, Cl$_2$SiPc, (HO)AlPc, (HO)GaPc, VOPc, TiOPc, MoOPc, GaPc-O-GaPc and corresponding derivatives of naphthalocyanine. However, the derivatives of phthalocyanine and naphthalocyanine are not limited to the compounds described above as the examples.

As the electron injecting material, a compound which has the ability to transport electrons, exhibits an excellent effect of electron injection from the cathode and an excellent effect of electron injection to the light emitting layer or the light emitting material, prevents transfer of excited components formed in the light emitting layer into the hole injecting layer and has excellent ability to form a thin film is preferable. Examples of the above compound include fluorenone, anthraquinodimethane, diphenoquinone, thiopyrane dioxide, oxazole, oxadiazole, triazole, imidazole, perylenetetracarboxylic acid, fluorenylidenemethane, anthraquinodimethane, anthrone and derivatives of these compounds. However, the above compound is not limited to the compounds described above as the examples. The charge injecting property can be improved by adding an electron accepting material to the hole injecting material or by adding an electron donating material to the electron injecting material.

In the organic EL device of the present invention, more effective electron injecting materials are metal complex compounds and five-membered derivatives containing nitrogen.

Examples of the metal complex compound include 8-hydroxyquinolinatolithium, bis(8-hydroxyquinolinato)zinc, bis(8-hydroxyquinolinato)copper, bis(8-hydroxyquinolinato)manganese, tris(8-hydroxyquinolinato)aluminum, tris (2-methyl-8-hydroxyquinolinato)-aluminum, tris(8-hydroxyquinilinato)gallium, bis(10-hydroxybenzo-[h]quinolinato) beryllium, bis(10-hydroxybenzo[h] quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum and bis(2-methyl-8-quinolinato)(2-naphtholato)gallium. However, the metal complex compound is not limited to the compounds described above as the examples.

Preferable examples of the five-membered derivative containing nitrogen include derivatives of oxazoles, thiazoles, thiadiazoles and triazoles. Specific examples include 2,5-bis(1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis [2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'tert-butylphenyl)-5-(4"-biphenyl)-1,3,4-triazole, 2,5-bis(1-naphthyl)-1,3,4-triazole and 1,4-bis[2-(5-phenyltriazolyl)] benzene. However, the five-membered derivative containing nitrogen is not limited to the compounds described above as the examples.

In the organic EL device of the present invention, the organic layer may contain at least one of light emitting materials, doping materials, hole injecting materials and electron injecting materials in the same layer in addition to any of the compounds represented by general formula [1], [1'] and [2] to [5]. In order to improve stability of the organic EL device of the present invention with respect to temperature, humidity and atmosphere, a protecting layer may be formed on the surface of the device or the entire device may be protected with silicon oil or a resin.

As the conductive material used for the anode of the organic EL device, a material having a work function of 4 eV or greater is suitable. Examples of such a material include carbon, aluminum, vanadium, iron, cobalt, nickel, tungsten, silver, gold, platinum, palladium, alloys of these metals, metal oxides used for ITO substrates and NESA substrates such as tin oxide and indium oxide and organic conductive resins such as polythiophene and polypyrrol. As the conductive material used for the cathode, a material having a work function smaller than 4 eV is suitable. Examples of such a material include magnesium, calcium, tin, lead, titanium, yttrium, lithium, ruthenium, manganese, aluminum and alloys of these metals. However, the materials used for the anode and the cathode are not limited to the materials described above as the examples. Typical examples of the alloy include alloys of magnesium and silver, alloys of magnesium and indium and alloys of lithium and aluminum. However, the alloy is not limited to these alloys described as the examples. The composition of the alloy is controlled by the temperature of the source of vapor deposition, the atmosphere and the degree of vacuum and can be adjusted suitably. The anode and the cathode may have a multi-layer structure having two or more layers, where necessary.

In the organic EL device, to achieve efficient light emission, it is preferable that at least one face of the device is sufficiently transparent in the wave length region of the emitted light. It is preferable that the substrate is also transparent. The transparent electrode is disposed in accordance with vapor deposition or sputtering using the above conductive material in a manner such that the prescribed transparency is surely obtained. It is preferable that the electrode disposed on the light emitting face has a transmittance of light of 10% or greater. The substrate is not particularly limited as long as the substrate has sufficient mechanical strength and strength at high temperatures and is transparent. Glass substrates or transparent films of resins may be used. Example of the transparent films of resins include films of polyethylene, ethylene-vinyl acetate copolymers, ethylene-vinyl alcohol copolymers, polypropylene, polystyrene, polymethyl methacrylate, polyvinyl chloride, polyvinyl alcohol, polyvinyl butyral, nylon, polyether ether ketones, polsulfones, polyether sulfones, tetrafluoroethylene-perfluoroalkyl vinyl ether copolymers, polyvinyl fluoride, tetrafluoroethylene-ethylene copolymers, tetrafluoroethylene-hexafluoropropylene copolymers, polychlorotrifluoro-ethylene, polyvinylidene fluoride, polyesters, polycarbonates, polyurethanes, polyether imides, polyimides and polypropylene.

Each layer of the organic EL device of the present invention can be formed suitably in accordance with a dry process of film formation such as vacuum vapor deposition, sputtering, plasma plating and ion plating or a wet process of film formation such as spin coating, dipping and flow coating. The thickness of the film is not particularly limited. However, it is necessary that the thickness be set at a suitable value. When the thickness is greater than the suitable value, a high voltage must be applied to obtain a prescribed output of light and the efficiency decreases. When the thickness is smaller than the suitable value, pin holes are formed and a sufficient luminance cannot be obtained even when the electric field is applied. In general, the suitable range of the thickness is 5 nm to 10 μm. A thickness in the range of 10 nm to 0.2 μm is preferable.

When the device is produced in accordance with a wet process, materials forming each layer are dissolved or dispersed in a suitable solvent such as ethanol, chloroform, tetrahydrofuran and dioxane and a film is formed from the solution or the suspension. The solvent is not particularly limited. In any organic thin layer, suitable resins and additives may be used to improve the property to form a film and to prevent formation of pin holes. Examples of the resin which can be used include insulating resins such as polystyrene, polycarbonates, polyarylates, polyesters, polyamides, polyurethanes, polysulfones, polymethyl methacrylate, polymethyl acrylate and cellulose; copolymers derived from these resins; photoconductive resins such as poly-N-vinylcarbazole and polysilane; and conductive resins such as polythiophene and polypyrrol. Examples of the additive include antioxidants, ultraviolet light absorbents and plasticizers.

As described above, when the compound of the present invention is used for the organic layer of the organic EL device, the organic EL device exhibiting excellent efficiency of light emission and heat resistance, having a long life and emitting bluish light having excellent purity of color can be obtained.

The organic EL device of the present invention can be used for a planar light emitting member such as a flat panel display of wall televisions, a back light for copiers, printers and liquid crystal displays, a light source of instruments, display panels and a marker light.

The present invention will be described more specifically with reference to Synthesis Examples and Examples in the following.

SYNTHESIS EXAMPLE 1

Compound 14

(1) Synthesis of 2,2'-dibromobiphenyl

Under an atmosphere of argon, 1,2-bromobenzene (25 g, 0.11 mole) was dissolved into anhydrous THF (240 ml) and the resultant solution was cooled at −67° C. in a dry ice/methanol bath. To the cooled solution, a hexane solution of n-butyllithium (1.50 mole/liter, 35 ml, 53 mmole, 0.5 eq) was slowly added dropwise over 5 minutes. The resultant mixture was stirred at −67° C. for 1 hour and then at the room temperature for 3 hours. To the obtained reaction mixture, a saturated aqueous solution of ammonium chloride (100 ml) was added. The formed organic layer was separated, washed with a saturated aqueous solution of sodium chloride (50 ml) and dried over anhydrous magnesium sulfate. Then, the solvent was removed by distillation and a brown liquid (about 19 g) was obtained. The obtained liquid was purified by the column chromatography (silica gel/hexane) and white needle crystals (9.5 g, 57%) were obtained.

1H-NMR (CDCl$_3$, TMS) δ: 7.2 to 7.4 (6H, m), 7.6 to 7.7 (2H, m)

(2) Synthesis of 2-phenyl-2'-bromobiphenyl

Under an atmosphere of argon, 2,2'-dibromobiphenyl (9.5 g, 30 mmole), phenylboronic acid (3.7 g, 30 mmole) and tetrakis(triphenylphosphine)palladium(0) (1.0 g, 0.87 mmole, 3% Pd) were dissolved into toluene (75 ml). To the obtained solution, an aqueous solution of sodium carbonate (9.7 g, 92 mmole, 3 eq/46 ml) was added. The resultant solution was heated under refluxing for 10 hours and left standing for one night. The formed organic layer was separated, washed with a saturated aqueous solution of sodium chloride (50 ml) and dried over anhydrous magnesium sulfate. Then, the solvent was removed by distillation and a dark yellow oil was obtained. The obtained oil was purified by the column chromatography (silica gel/hexane, hexane+3% dichloromethane and hexane+5% dichloromethane, successively) and a colorless oil (6.5 g, 70%) was obtained.

$^1$H-NMR (CDCl$_3$, TMS) δ: 6.6 to 6.7 (1H, m), 7.0 to 7.6 (12H, m)

(3) Synthesis of 9,10-bis(2-(2-phenylphenyl)phenyl)-9,10-dihydroxy-9,10-dihydroanthracene Under an atmosphere of argon, 2-phenyl-2'-bromobiphenyl (6.5 g, 21 mmole, 2.5 eq) was dissolved into a mixed solvent composed of anhydrous toluene (25 ml) and anhydrous tetrahydrofuran (THF) (25 ml) and the resultant solution was cooled at −30° C. in a dry ice/methanol bath. To the cooled solution, a hexane solution of n-butyllithium (1.50 mole/liter, 15 ml, 23 mmole, 1.1 eq) was added and the resultant solution was stirred at −20° C. for 1 hour. To the obtained solution, anthraquinone (1.7 g, 8.2 mmole) was added and the resultant mixture was stirred at −20° C. for 1 hour and at the room temperature for 2 hours and left standing for one night. To the obtained reaction mixture, a saturated aqueous solution of ammonium chloride (20 ml) was added. The formed solid was separated by filtration, washed with water, methanol and acetone and a white solid (2.9 g, 53%) was obtained.

$^1$H-NMR (CDCl$_3$, TMS) δ: 0.47 (2H, s), 5.7 to 5.8 (2H, m), 6.3 to 7.4 (30H, m), 8.3 to 8.4 (2H, m)

(4) Synthesis of 9,10-bis(2-(2-phenylphenyl)phenyl)anthracene (Compound 14)

9,10-bis(2-(2-Phenylphenyl)phenyl)-9,10-dihydroxy-9,10-dihydroanthracene (2.9 g, 4.3 mmole) was suspended in acetic acid (45 ml). To the resultant suspension, a 57% hydroiodic acid (6 ml, 45 mmole, 10 eq) was added and the obtained mixture was stirred at 100° C. for 6 hours. To the reaction mixture, a 50% aqueous solution of hypophosphorous acid (30 ml) was added. The formed solid was separated by filtration and washed with water, methanol and acetone and a light yellow solid (2.4 g, 88%) was obtained.

$^1$H-NMR (CDCl$_3$, TMS) δ: 6.7 to 7.5 (34H, m), all-H

SYNTHESIS EXAMPLE 2

Compound 15

(1) Synthesis of 1-(2-bromophenyl)naphthalene

Under an atmosphere of argon, 2-bromoiodobenzene (7.0 g, 25 mmole), naphthaleneboronic acid (4.0 g, 23 mmole) and tetrakis(triphenylphosphine)palladium(0) (0.5 g, 0.43 mmole, 1.7% Pd) were dissolved into toluene (50 ml). To the obtained solution, an aqueous solution of sodium carbonate (7.3 g, 69 mmole, 3 eq/35 ml) was added. The resultant solution was heated under refluxing for 10 hours and left standing for one night. The formed organic layer was separated, washed with a saturated aqueous solution of sodium chloride (50 ml) and dried with anhydrous magnesium sulfate. Then, the solvent was removed by distillation and a yellow oil was obtained. The obtained oil was purified by the column chromatography (silica gel/hexane, hexane+3% dichloromethane and hexane+10% dichloromethane, successively) and white needle crystals (5.4 g, 83%) were obtained.

$^1$H-NMR (CDCl$_3$, TMS) δ: 7.3 to 7.8 (9H, m), 7.90 (2H, dd, J=8 Hz, 2 Hz)

(2) Synthesis of 9,10-bis(2-(1-naphthyl)phenyl)-9,10-dihydroxy-9,10-dihydroanthracene Under an atmosphere of argon, 1-(2-bromophenyl)naphthalene (5.4 g, 19 mmole, 2.8 eq) was dissolved into a mixed solvent composed of anhydrous toluene (25 ml) and anhydrous THF (25 ml) and the resultant solution was cooled at −40° C. in a dry ice/methanol bath. To the cooled solution, a hexane solution of n-butyllithium (1.50 mole/liter, 14 ml, 21 mmole, 1.1 eq) was added and the resultant solution was stirred at −20° C. for 1 hour. To the obtained solution, anthraquinone (1.4 g, 6.7 mmole) was added and the resultant mixture was stirred at −20° C. for 1 hour and at the room temperature for 3 hours and left standing for one night. To the obtained reaction mixture, a saturated aqueous solution of ammonium chloride (20 ml) was added. The formed solid was separated by filtration, washed with water, methanol and acetone and a white solid (3.5 g, 85%) was obtained.

$^1$H-NMR (CDCl$_3$, TMS) δ: −0.20 (2H, s), 5.76 (2H, dd, J=13 Hz, 7 Hz), 6.2 to 7.7 (26H, m), 8.43 (2H, d, J=8 Hz)

(3) Synthesis of 9,10-bis(2-(1-naphthyl)phenyl)anthracene (Compound 15)

9,10-bis(2-(1-Naphthyl)phenyl)-9,10-dihydroxy-9,10-dihydroanthracene (3.5 g, 5.7 mmole) was suspended in acetic acid (80 ml). To the resultant suspension, a 57% hydroiodic acid (15 ml, 0.11 mole, 20 eq) was added and the obtained mixture was stirred at 100° C. for 7 hours. To the reaction mixture, a 50% aqueous solution of hypophosphorous acid (30 ml) was added. The formed solid was separated by filtration and washed with water, methanol and acetone and a white solid (3.2 g, 96%) was obtained.

$^1$H-NMR (CDCl$_3$, TMS) δ: 6.7 to 7.5 (30H, m), all-H

SYNTHESIS EXAMPLE 3

Compound 17

(1) Synthesis of 9-phenanthreneboronic acid

Under an atmosphere of argon, 9-bromophenanthrene (15 g, 58 mmole) was dissolved into anhydrous ether (150 ml) and the resultant solution was cooled at −35° C. in a dry ice/methanol bath. To the cooled solution, a hexane solution of n-butyllithium (1.50 mole/liter, 43 ml, 65 mmole) was added dropwise and the resultant mixture was stirred at −20° C. for 1 hour. After the reaction mixture was cooled at −67° C., a solution (30 ml) of triisopropoxyborane (37 ml, 0.16 mole, 2.8 eq) in anhydrous ether was added the resultant mixture was stirred at −65° C. for 1 hour and at the room temperature for 2 hours and left standing for one night. To the obtained reaction mixture, a 10% hydrochloric acid (150 ml) was added. After the resultant mixture was stirred at the room temperature for 1 hour, the formed organic layer was separated, washed with a saturated aqueous solution of sodium chloride (50 ml) and dried with anhydrous magnesium sulfate. The solid obtained after removing the solvent by distillation was washed with hexane and a white solid (10 g, 78%) was obtained.

$^1$H-NMR (CDCl$_3$, TMS) δ: 7.6 to 7.9 (5H, m), 8.17 (1H, s), 8.5 to 8.8 (3H, m)

(2) Synthesis of 9-(3-bromophenyl)phenanthrene

Under an atmosphere of argon, 3-bromoiodobenzene (7.0 g, 25 mmole), phenanthreneboronic acid (5.0 g, 23 mmole) and tetrakis-(triphenylphosphine)palladium(0) (0.5 g, 0.43 mmole, 1.7% Pd) were dissolved into toluene (100 ml). To the obtained solution, an aqueous solution of sodium carbonate (7.3 g, 69 mmole, 3 eq/35 ml) was added and the resultant solution was heated under refluxing for 10 hours and left standing for one night. The formed organic layer was separated, washed with a saturated aqueous solution of sodium chloride (50 ml) and dried with anhydrous magnesium sulfate. Then, the solvent was removed by distillation and a yellow oil was obtained. The obtained oil was purified by the column chromatography (silica gel/hexane, hexane+3% dichloromethane and hexane+5% dichloromethane, successively) and white needle crystals (6.5 g, 85%) were obtained.

$^1$H-NMR (CDCl$_3$, TMS) δ: 7.3 to 8.7 (11H, m), 8.76 (2H, d, J=7 Hz)

(3) Synthesis of 9,10-bis(3-(9-phenanthryl)phenyl)-9,10-dihydroxy-9,10-dihydroanthracene Under an atmosphere of argon, 1-(3-bromophenyl)naphthalene (6.5 g, 20 mmole, 2.8 eq) was dissolved into a mixed solvent composed of anhydrous toluene (25 ml) and anhydrous THF (25 ml) and the resultant solution was cooled at −25° C. in a dry ice/methanol bath. To the cooled solution, a hexane solution of n-butyllithium (1.50 mole/liter, 15 ml, 23 mmole, 1.1 eq) was added and the resultant solution was stirred at −20° C. for 1 hour. To the obtained mixture, anthraquinone (1.5 g, 7.2 mmole) was added and the resultant mixture was stirred at −20° C. for 1 hour and at the room temperature for 3 hours and left standing for one night. To the obtained reaction mixture, a saturated aqueous solution of ammonium chloride (20 ml) was added. The formed solid was separated by filtration and washed with water, methanol and acetone and a white solid (5.9 g, quant.) was obtained.

$^1$H-NMR (CDCl$_3$, TMS) δ: −0.16 (2H, s), 6.06 (2H, s), 6.4 to 7.0 (12H, m), 7.1 to 7.7 (12H, m), 8.20 (2H, dd, J=8 Hz, 2 Hz), 8.4 to 8.6 (6H, m)

(4) Synthesis of 9,10-bis(3-(9-phenanthryl)phenyl)anthracene (Compound 17)

9,10-bis(3-(9-Phenanthryl)phenyl)-9,10-dihydroxy-9,10-dihydroanthracene (5.2 g, 7.3 mmole) was suspended in acetic acid (120 ml). To the resultant suspension, a 57% hydroiodic acid (10 ml, 77 mmole, 10 eq) was added and the obtained mixture was stirred at 100° C. for 6 hours. To the reaction mixture, a 50% aqueous solution of hypophosphorous acid (40 ml) was added. The formed solid was separated by filtration and washed with water, methanol and acetone and a white solid (5.0 g, quant.) was obtained.

$^1$H-NMR (CDCl$_3$, TMS) δ: 7.0 to 8.5 (34H, m), all-H

SYNTHESIS EXAMPLE 4

Compound 20

(1) Synthesis of 1-(4-bromophenyl)pyrene

Under an atmosphere of argon, 4-bromoiodobenzene (7.0 g, 25 mmole), 1-pyreneboronic acid (5.7 g, 23 mmole) and tetrakis(triphenylphosphine)palladium(0) (0.5 g, 0.43 mmole, 1.7% Pd) were dissolved into toluene (50 ml). To the obtained solution, an aqueous solution of sodium carbonate (7.3 g, 69 mmole, 3 eq/35 ml) was added. The resultant solution was heated under refluxing for 10 hours and left standing for one night. The formed organic layer was separated, washed with a saturated aqueous solution of sodium chloride (50 ml) and dried with anhydrous magnesium sulfate. Then, the solvent was removed by distillation and a yellow oil was obtained. The obtained oil was purified by the column chromatography (silica gel/hexane, hexane+3% dichloromethane and hexane+10% dichloromethane, successively) and white needle crystals (6.6 g, 80%) were obtained.

$^1$H-NMR (CDCl$_3$, TMS) δ: 7.3 to 7.8 (11H, m), 7.90 (2H, d, J=8 Hz)

(2) Synthesis of 9,10-bis(4-(1-pyrenyl)phenyl)-9,10-dihydroxy-9,10-dihydroanthracene Under an atmosphere of argon, 1-(2-bromophenyl)pyrene (6.6 g, 18 mmole, 2.8 eq) was dissolved into a mixed solvent composed of anhydrous toluene (25 ml) and anhydrous THF (25 ml) and the resultant solution was cooled at −40° C. in a dry ice/methanol bath. To the cooled solution, a hexane solution of n-butyllithium (1.50 mole/liter, 14 ml, 21 mmole, 1.1 eq) was added and the obtained solution was stirred at −20° C. for 1 hour. To the obtained mixture, anthraquinone (1.4 g, 6.7 mmole) was added and the resultant mixture was stirred at −20° C. for 1 hour and at the room temperature for 3 hours and left standing for one night. To the obtained reaction mixture, a saturated aqueous solution of ammonium chloride (20 ml) was added. The formed solid was separated by filtration and washed with water, methanol and acetone and a white solid (4.5 g, 88%) was obtained.

$^1$H-NMR (CDCl$_3$, TMS) δ: −0.20 (2H, s), 5.76 (2H, dd, J=13 Hz, 7 Hz), 6.2 to 7.7 (30H, m), 8.43 (2H, d, J=8 Hz)

(3) Synthesis of 9,10-bis(4-(1-pyrenyl)phenyl)anthracene (Compound 20)

9,10-bis(4-(1-Pyrenyl)phenyl)-9,10-dihydroxy-9,10-dihydroanthracene (4.5 g, 5.9 mmole) was suspended in acetic acid (80 ml). To the resultant suspension, a 57% hydroiodic acid (15 ml, 0.11 mole, 20 eq) was added and the obtained mixture was stirred at 100° C. for 7 hours. To the reaction mixture, a 50% aqueous solution of hypophosphorous acid (30 ml) was added. The formed solid was separated by filtration and washed with water, methanol and acetone and a white solid (3.9 g, 90%) was obtained.

$^1$H-NMR (CDCl$_3$, TMS) δ: 6.7 to 7.5 (30H, m), all-H

SYNTHESIS EXAMPLE 5

Compound 22

(1) Synthesis of 2-biphenylboronic acid

Under an atmosphere of argon, 2-bromobiphenyl (20 g, 86 mmole) was dissolved into anhydrous ether (200 ml) and the resultant solution was cooled at −35° C. in a dry ice/methanol bath. To the cooled solution, a hexane solution of n-butyllithium (1.50 mole/liter, 63 ml, 95 mmole) was added dropwise and the resultant mixture was stirred at −20° C. for 1 hour. After the reaction mixture was cooled at −67° C., a solution (50 ml) of triisopropoxyborane (50 ml, 0.22 mole, 2.5 eq) in anhydrous ether was added and the resultant mixture was stirred at −65° C. for 1 hour and at the room temperature for 2 hours and left standing for one night. To the obtained reaction mixture, a 10% hydrochloric acid (200 ml) was added. After the resultant mixture was stirred at the room temperature for 1 hour, the formed organic layer was separated, washed with a saturated aqueous solution of sodium chloride (50 ml) and dried with anhydrous magnesium sulfate. The solid obtained after removing the solvent by distillation was washed with hexane and a white solid (11 g, 62%) was obtained.

$^1$H-NMR (CDCl$_3$, TMS) δ: 6.74(1H, d, J=7 Hz), 7.1 to 7.4 (8H, m)

(2) Synthesis of 2-(4-bromophenyl)biphenyl

Under an atmosphere of argon, 2-bromoiodobenzene (7.9 g, 25 mmole), biphenylboronic acid (5.0 g, 25 mmole) and tetrakis(triphenylphosphine)palladium(0) (0.5 g, 0.43 mmole, 1.7% Pd) were dissolved into toluene (60 ml). To the obtained solution, an aqueous solution of sodium carbonate (8.0 g, 75 mmole, 3 eq/40 ml) was added. The resultant solution was heated under refluxing for 10 hours and left standing for one night. The formed organic layer was separated, washed with a saturated aqueous solution of sodium chloride (50 ml) and dried with anhydrous magnesium sulfate. Then, the solvent was removed by distillation and a yellow oil was obtained. The obtained oil was purified by the column chromatography (silica gel/hexane, hexane+3% dichloromethane and hexane+5% dichloromethane, successively) and white needle crystals (6.8 g, 88%) were obtained.

$^1$H-NMR (CDCl$_3$, TMS) δ: 7.3 to 8.7 (11H, m), 8.76 (2H, d, J=7 Hz)

(3) Synthesis of 9,10-bis(4-(2-phenylphenyl)phenyl)-9,10-dihydroxy-9,10-dihydroanthracene Under an atmosphere of argon, 2-(4-bromophenyl)biphenyl (6.8 g, 22 mmole, 2.5 eq) was dissolved into a mixed solvent composed of anhydrous toluene (25 ml) and anhydrous THF (25 ml) and the resultant solution was cooled at −30° C. in a dry ice/methanol bath. To the cooled solution, a hexane solution of n-butyllithium (1.50 mole/liter, 15 ml, 23 mmole, 1.1 eq) was added and the resultant solution was stirred at −20° C. for 1 hour. To the obtained mixture, anthraquinone (1.7 g, 8.2 mmole) was added and the resultant mixture was stirred at −20° C. for 1 hour and at the room temperature for 2 hours and left standing for one night. To the obtained reaction mixture, a saturated aqueous solution of ammonium chloride (20 ml) was added. The formed solid was separated by filtration and washed with water, methanol and acetone and a white solid (4.9 g, 89%) was obtained.

$^1$H-NMR (CDCl$_3$, TMS) δ: 5.7 to 5.8 (2H, m), 6.3 to 7.4 (30H, m), 8.3 to 8.4 (2H, m)

(4) Synthesis of 9,10-bis(4-(2-phenylphenyl)phenyl)anthracene (Compound 22)

9,10-bis(4-(2-Phenylphenyl)phenyl)-9,10-dihydroxy-9,10-dihydroanthracene (4.9 g, 7.3 mmole) was suspended in acetic acid (70 ml). To the resultant suspension, a 57% hydroiodic acid (10 ml, 77 mmole, 10 eq) was added and the obtained mixture was stirred at 100° C. for 6 hours. To the reaction mixture, a 50% aqueous solution of hypophosphorous acid (50 ml) was added. The formed solid was separated by filtration and washed with water, methanol and acetone and a light yellow solid (4.6 g, 88%) was obtained.

$^1$H-NMR (CDCl$_3$, TMS) δ: 6.7 to 7.5 (34H, m), all-H

SYNTHESIS EXAMPLE 6

Synthesis of Compound 1

(1) Synthesis of 9,10-bis(4-(3-phenylphenyl)phenyl)-9,10-dihydroxy-9,10-dihydroanthracene Under an atmosphere of argon, 3-(4-bromophenyl)biphenyl (6.8 g, 22 mmole, 2.5 eq) was dissolved into a mixed solvent composed of anhydrous toluene (25 ml) and anhydrous THF (25 ml) and the resultant solution was cooled at −30° C. in a dry ice/methanol bath. To the cooled solution, a hexane solution of n-butyllithium (1.50 mole/liter, 15 ml, 23 mmole, 1.1 eq) was added and the resultant mixture was stirred at −20° C. for 1 hour. To the obtained solution, anthraquinone (1.7 g, 8.2 mmole) was added and the resultant mixture was stirred at −20° C. for 1 hour and at the room temperature for 2 hours and left standing for one night. To the obtained reaction mixture, a saturated aqueous solution of ammonium chloride (20 ml) was added. The formed solid was separated by filtration and washed with water, methanol and acetone and a white solid (5.0 g, 91%) was obtained.

$^1$H-NMR (CDCl$_3$, TMS) δ: 5.7 to 5.8 (2H, m), 6.3 to 7.4 (30H, m), 8.3 to 8.4 (2H, m)

(2) Synthesis of 9,10-bis(4-(3-phenylphenyl)phenyl)anthracene (Compound 1)

9,10-bis(4-(3-Phenylphenyl)phenyl)-9,10-dihydroxy-9,10-dihydroanthracene (4.9 g, 7.3 mmole) was suspended in acetic acid (70 ml). To the resultant suspension, a 57% hydroiodic acid (10 ml, 77 mmole, 10 eq) was added and the obtained mixture was stirred at 100° C. for 6 hours. To the reaction mixture, a 50% aqueous solution of hypophosphorous acid (50 ml) was added. The formed solid was separated by filtration and washed with water, methanol and acetone and a light yellow solid (4.1 g, 79%) was obtained.

$^1$H-NMR (CDCl$_3$, TMS) δ: 6.7 to 7.5 (34H, m), all-H

SYNTHESIS EXAMPLE 7

Synthesis of Compound 2

(1) Synthesis of 9,10-bis(4-(3,5-diphenylphenyl)phenyl)-9,10-dihydroxy-9,10-dihydroanthracene Under an atmosphere of argon, 1,3-diphenyl-5-(4-bromophenyl)-benzene (8.5 g, 22 mmole, 2.5 eq) was dissolved into a mixed solvent composed of anhydrous toluene (25 ml) and anhydrous THF (25 ml) and the resultant solution was cooled at −30° C. in a dry ice/methanol bath. To the cooled solution, a hexane solution of n-butyllithium (1.50 mole/liter, 15 ml, 23 mmole, 1.1 eq) was added and the resultant mixture was stirred at −20° C. for 1 hour. To the obtained solution, anthraquinone (1.7 g, 8.2 mmole) was added and the obtained mixture was stirred at −20° C. for 1 hour and at the room temperature for 2 hours and left standing for one night. To the obtained reaction mixture, a saturated aqueous solution of ammonium chloride (20 ml) was added. The formed solid was separated by filtration and washed with water, methanol and acetone and a white solid (16 g, 90%) was obtained.

$^1$H-NMR (CDCl$_3$, TMS) δ: 5.7 to 5.8 (2H, m), 6.3 to 7.4 (30H, m), 8.3 to 8.4 (2H, m)

(2) Synthesis of 9,10-bis(4-(3,5-diphenylphenyl)phenyl)anthracene (Compound 2)

9,10-bis(4-(3,5-Diphenylphenyl)phenyl)-9,10-dihydroxy-9,10-dihydroanthracene (6.0 g, 7.3 mmole) was suspended in acetic acid (70 ml). To the resultant suspension, a 57% hydroiodic acid (10 ml, 77 mmole, 10 eq) was added and the obtained mixture was stirred at 100° C. for 6 hours. To the reaction mixture, a 50% aqueous solution of hypophosphorous acid (50 ml) was added. The formed solid was separated by filtration and washed with water, methanol and acetone and a light yellow solid (5.3 g, 93%) was obtained.

1H-NMR (CDCl$_3$, TMS) δ: 6.7 to 7.5 (34H, m), all-H

SYNTHESIS EXAMPLE 8

Synthesis of Compound 3

(1) Synthesis of 9,10-bis(4-(2-naphthyl)phenyl)-9,10-dihydroxy-9,10-dihydroanthracene Under an atmosphere of argon, 2-(4-bromophenyl)naphthalene (5.4 g, 19 mmole, 2.8 eq) was dissolved into a mixed solvent composed of anhydrous toluene (25 ml) and anhydrous THF (25 ml) and the resultant solution was cooled at −40° C. in a dry ice/methanol bath. To the cooled solution, a hexane solution of n-butyllithium (1.50 mole/liter, 14 ml, 21 mmole, 1.1 eq) was added and the resultant mixture was stirred at −20° C. for 1 hour. To the resultant solution, anthraquinone (1.4 g, 6.7 mmole) was added and the obtained mixture was stirred at −20° C. for 1 hour and at the room temperature for 3 hours and left standing for one night. To the obtained reaction mixture, a saturated aqueous solution of ammonium chloride (20 ml) was added. The formed solid was separated by filtration and washed with water, methanol and acetone and a white solid (3.7 g, 91%) was obtained.

$^1$H-NMR (CDCl$_3$, TMS) δ: −0.20 (2H, s), 5.76 (2H, dd, J=13 Hz, 7 Hz), 6.2 to 7.7 (26H, m), 8.43 (2H, d, J=8 Hz)

(2) Synthesis of 9,10-bis(4-(2-naphthyl)phenyl)anthracene (Compound 3)

9,10-bis(4-(2-Naphthyl)phenyl)-9,10-dihydroxy-9,10-dihydroanthracene (3.5 g, 5.7 mmole) was suspended in acetic acid (80 ml). To the resultant suspension, a 57% hydroiodic acid (15 ml, 0.11 mole, 20 eq) was added and the obtained mixture was stirred at 100° C. for 7 hours. To the reaction mixture, a 50% aqueous solution of hypophosphorous acid (30 ml) was added. The formed solid was separated by filtration and washed with water, methanol and acetone and a white solid (3.3 g, 98%) was obtained.

$^1$H-NMR (CDCl$_3$, TMS) δ: 6.7 to 7.5 (30H, m), all-H

SYNTHESIS EXAMPLE 9

Compound 25

(1) Synthesis of 1-(2,2-diphenylvinyl)-3,5-dibromobenzene

Under an atmosphere of argon, 3,5-dibromobenzaldehyde (12.1 g, 46 L mmole) and diethyl diphenylmethylphosphonate (15 g, 49 mmole, 1.1 eq) were dissolved into dimethyl sulfoxide (DMSO) (60 ml). To the resultant solution, potassium t-butoxide (6.2 g, 55 mmole, 1.2 eq) was added in small portions and the obtained solution was stirred at the room temperature for 9 hours and left standing for one night. After water (60 ml) was added, the reaction mixture was subjected to extraction with ethyl acetate (250 ml). The obtained organic layer was washed with water (100 ml) and a saturated aqueous solution of sodium chloride (50 ml) and dried with magnesium sulfate. Then, the solvent was removed by distillation and a deep brown oil was obtained. The obtained oil was purified by the column chromatography (silica gel/hexane and hexane+3% dichloromethane, successively) and a white solid (14.0 g, 74%) was obtained.

$^1$H-NMR (CDCl$_3$, TMS) δ: 6.80 (1H, s), 7.03 (2H, d, J=2 Hz), 7.3 to 7.4 (11H, m)

(2) Synthesis of 1-(2,2-diphenylvinyl)-3-phenyl-5-bromobenzene

Under an atmosphere of argon, 1-(2,2-diphenylvinyl)-3,5-dibromobenzene (7.0 g, 17 mmole), phenylboronic acid (2.1 g, 17 mmole) and tetrakis(triphenylphosphine)palladium(0) (0.4 g, 0.35 mmole, 2% Pd) were dissolved into toluene (40 ml). To the obtained solution, a 2 M aqueous solution of sodium carbonate (25 ml, 51 mmole, 3 eq) was added. The resultant solution was heated under refluxing for 10 hours and left standing for one night. The formed organic layer was separated, washed with a saturated aqueous solution of sodium chloride (30 ml) and dried with anhydrous magnesium sulfate. Then, the solvent was removed by distillation and a yellow oil was obtained. The obtained oil was purified by the column chromatography (silica gel/hexane, hexane+3% dichloromethane and hexane+10% dichloromethane, successively) and white needle crystals (3.9 g, 56%) were obtained.

$^1$H-NMR (CDCl$_3$, TMS) δ: 6.94 (1H, s), 7.1 to 7.5 (18H, m)

(3) Synthesis of 9,10-bis(3-(2,2-diphenylvinyl)phenyl-5-phenyl)-9,10-dihydroxy-9,10-dihydroanthracene Under an atmosphere of argon, 1-(2,2-diphenylvinyl)-3-phenyl-5-bromobenzene (3.9 g, 9.5 mmole, 2.7 eq) was dissolved into a mixed solvent composed of anhydrous toluene (20 ml) and anhydrous THF (20 ml) and the resultant solution was cooled at −40° C. in a dry ice/methanol bath. To the cooled solution, a hexane solution of n-butyllithium (1.60 mole/liter, 6 ml, 9.6 mmole, 1.0 eq) was added and the resultant mixture was stirred at −20° C. for 1 hour. To the obtained solution, anthraquinone (0.7 g, 3.4 mmole) was added and the resultant mixture was stirred at −20° C. for 1 hour and at the room temperature for 7 hours and left standing for one night. To the obtained reaction mixture, a saturated aqueous solution of ammonium chloride (50 ml) was added and the reaction was deactivated. The formed organic layer was separated, washed with a saturated aqueous solution of sodium chloride (30 ml) and dried with anhydrous magnesium sulfate. Then, the solvent was removed by distillation and a yellow oil was obtained. The obtained oil was purified by the column chromatography (silica gel/hexane, hexane+50% dichloromethane, dichloromethane and dichloromethane+3% methanol, successively) and a light yellow amorphous solid (2.0 g, 67%) was obtained.

$^1$H-NMR (CDCl$_3$, TMS) δ: 2.56 (2H, s), 6.5 to 6.6 (4H, m), 6.8 to 7.4 (34H, m), 7.41 (4H, dd, J=6 Hz, 3 Hz), 7.71 (4H, dd, J=6 Hz, 3 Hz)

(4) Synthesis of 9,10-bis(3-(2,2-diphenylvinyl)phenyl-5-phenyl)-anthracene (Compound 25)

9,10-bis(3-(2,2-Diphenylvinyl)phenyl-5-phenyl)-9,10-dihydroxy-9,10-dihydroanthracene (2.0 g, 2.3 mmole) was dissolved into acetic acid (25 ml). To the resultant solution, potassium iodide (1.5 g, 90 mmole, 4 eq) was added and the obtained solution was stirred for 3 hours. To the reaction mixture, a 50% aqueous solution of phosphinic acid was added and the reaction was deactivated. The formed solid was separated by filtration and washed with water, methanol and acetone and a white solid (1.4 g, 73%) was obtained.

$^1$H-NMR (CDCl$_3$, TMS) δ: 7.2 to 7.4 (42H, m), 7.65 (4H, dd, J=7 Hz, 3 Hz)

The solid obtained above (1.4 g) was purified by sublimation at 380° C. under 10$^{-6}$ Torr for 1 hour and a light yellow solid (0.8 g) was obtained.

FDMS: calc. for C$_{66}$H$_{46}$=838, found m/z=838 (M$^+$, 4)
λmax, 398, 358, 306 nm (PhMe)
Fmax, 416, 435 nm (PhMe, λex=395 nm)
Eg=3.00 eV
Ip=5.87 eV (51 Y/eV, 100 nW)
Tg=130° C.

SYNTHESIS EXAMPLE 10

Compound 26

(1) Synthesis of 1-(2,2-diphenylvinyl)-3-(1-naphthyl)-5-bromobenzene

Under an atmosphere of argon, 1-(2,2-diphenylvinyl)-3,5-dibromobenzene (8.3 g, 20 mmole), 1-naphthaleneboronic acid (3.4 g, 20 mmole) and tetrakis(triphenylphosphine)palladium(0) (0.46 g, 0.4 mmole, 2% Pd) were dissolved into toluene (50 ml). To the obtained solution, a 2 M aqueous solution of sodium carbonate (30 ml, 60 mmole, 3 eq) was added. The resultant solution was heated under refluxing for 10 hours and left standing for one night. The formed organic layer was separated, washed with a saturated aqueous solution of sodium chloride (50 ml) and dried with anhydrous magnesium sulfate. Then, the solvent was removed by distillation and a yellow oil was obtained. The obtained oil was purified by the column chromatography (silica gel/hexane, hexane+3% dichloromethane and hexane+10% dichloromethane, successively) and a white glass solid (5.5 g, 60%) was obtained.

$^1$H-NMR (CDCl$_3$, TMS) δ: 6.96 (1H, s), 7.1 to 7.6 (18H, m), 7.8 to 7.9 (2H, m)

(2) Synthesis of 9,10-bis(3-(2,2-diphenylvinyl)phenyl-5-(1-naphthyl))-9,10-dihydroxy-9,10-dihydroanthracene Under an atmosphere of argon, 1-(2,2-diphenylvinyl)-3-(1-naphthyl)-5-bromobenzene (5.5 g, 12 mmole, 2.7 eq) was dissolved into a mixed solvent composed of anhydrous toluene (30 ml) and anhydrous THF (30 ml) and the resultant solution was cooled at −30° C. in a dry ice/methanol bath. To the cooled solution, a hexane solution of n-butyllithium (1.60 mole/liter, 8 ml, 13 mmole, 1.0 eq) was added and the resultant mixture was stirred at −20° C. for 1 hour. To the obtained mixture, anthraquinone (0.9 g, 4.4 mmole) was added and the resultant mixture was stirred at −20° C. for 1 hour and at the room temperature for 7 hours and left standing for one night. To the obtained reaction mixture, a saturated aqueous solution of ammonium chloride (50 ml) was added and the reaction was deactivated. The formed organic layer was separated, washed with a saturated aqueous solution of sodium chloride (30 ml) and dried with anhydrous magnesium sulfate. Then, the solvent was removed by distillation and a yellow oil was obtained. The obtained oil was purified by the column chromatography (silica gel/hexane+50% dichloromethane and dichloromethane, successively) and a white amorphous solid (2.7 g, 63%) was obtained.

$^1$H-NMR (CDCl$_3$, TMS) δ: 2.56 (2H, s), 6.5 to 6.8 (6H, m), 6.9 to 7.5 (36H, m), 7.6–7.8 (8H, m)

(3) Synthesis of 9,10-bis(3-(2,2-diphenylvinyl)phenyl-5-(1-naphthyl))-anthracene (Compound 26)

9,10-bis(3-(2,2-Diphenylvinyl)phenyl-5-(1-naphthyl))-9,10-dihydroxy-9,10-dihydroanthracene (2.7 g, 2.8 mmole) was dissolved into acetic acid (30 ml). To the resultant solution, potassium iodide (1.8 g, 11 mmole, 4 eq) was added and the obtained solution was stirred for 3 hours. To the reaction mixture, a 50% aqueous solution of phosphinic acid (40 ml) was added and the reaction was deactivated. The formed solid was separated by filtration and washed with water, methanol and acetone and a white solid (2.0 g, 78%) was obtained.

$^1$H-NMR (CDCl$_3$, TMS) δ: 7.2 to 7.5 (40H, m), 7.7 to 7.9 (10H, m)

The solid obtained above (2.0 g) was purified by sublimation at 400° C. under 10$^{-6}$ Torr for 1 hour and a light yellow solid (1.2 g) was obtained.

FDMS: calc. for C$_{74}$H$_{50}$=938, found m/z=938 (M$^+$, 100), 469 (M$^{2+}$, 6)
λmax, 398, 377, 358 nm (PhMe)
Fmax, 418, 436 nm (PhMe, λex=395 nm)
Eg=3.00 eV
Ip=5.86 eV (34 Y/eV, 100 nW)
Tg=132° C.

SYNTHESIS EXAMPLE 11

Compound 33

(1) Synthesis of 2-t-butyl-9,10-bis(4-(2,2-diphenylvinyl)phenyl-9,10-dihydroxy-9,10-dihydroanthracene Under an atmosphere of argon, 4-(2,2-diphenylvinyl)bromobenzene (5.0 g, 15 mmole, 2.6 eq) was dissolved into a mixed solvent composed of anhydrous toluene (25 ml) and anhydrous THF (25 ml) and the resultant solution was cooled at −40° C. in a dry ice/methanol bath. To the cooled solution, a hexane solution of n-butyllithium (1.60 mole/liter, 10 ml, 16 mmole, 1.1 eq) was added and the resultant mixture was stirred at −20° C. for 1 hour. To the obtained mixture, 2-(t-butyl)anthraquinone (1.5 g, 5.7 mmole) was added and the resultant mixture was stirred at −20° C. for 1 hour and at the room temperature for 7 hours and left standing for one night. To the obtained reaction mixture, a saturated aqueous solution of ammonium chloride (50 ml) was added and the reaction was deactivated. The formed organic layer was separated, washed with a saturated aqueous solution of sodium chloride (30 ml) and dried with anhydrous magnesium sulfate. Then, the solvent was removed by distillation and a yellow oil was obtained. The obtained oil was purified by the column chromatography (silica gel/hexane+50% dichloromethane, dichloromethane and dichloromethane+1% methanol, successively) and a white amorphous solid (3.3 g, 75%) was obtained.

$^1$H-NMR (CDCl$_3$, TMS) δ: 1.29 (9H, s), 2.65 (1H, s), 2.71 (1H, s), 6.68 (9H, s), 6.84 (2H, s), 7.1 to 7.4 (23H, m), 7.5–7.7 (4H, m)

(2) Synthesis of 3-t-butyl-9,10-bis(4-(2,2-diphenylvinyl)phenyl)-anthracene (Compound 33)

2-t-Butyl-9,10-bis(4-(2,2-diphenylvinyl)phenyl)-9,10-dihydroxy-9,10-dihydroanthracene (3.3 g, 4.3 mmole) was dissolved into acetic acid (30 ml). To the resultant solution, potassium iodide (1.9 g, 11 mmole, 2.7 eq) and sodium phosphinate monohydrate (0.6 g, 5.7 mmole) were added and the obtained mixture was stirred for 2 hours. The reaction mixture was filtered and washed with water, methanol and acetone and a light yellow solid (2.8 g, 88%) was obtained.

$^1$H-NMR (CDCl$_3$, TMS) δ: 1.28 (9H, s), 7.14 (2H, s), 7.2 to 7.5 (30H, m), 7.6 to 7.7 (5H, m)

The solid obtained above (2.8 g) was purified by sublimation at 360° C. under 10$^{-6}$ Torr for 1 hour and a light yellow solid (2.2 g) was obtained.

FDMS: calc. for C$_{58}$H$_{46}$=742, found m/z=742 (M$^+$, 100), 371 (M$^{2+}$, 4)

λmax, 397, 379, 360, 310 nm (PhMe)
Fmax, 450 nm (PhMe, λex=397 nm)
Eg=2.92 eV
Ip=5.71 eV (39 Y/eV, 100 nW)
Tg=105° C.

SYNTHESIS EXAMPLE 12

Compound 34

(1) Synthesis of 2-phenylanthraquinone

Under an atmosphere of argon, 2-chloroanthraquinone (5.0 g, 21 mmole), phenylboronic acid (2.8 g, 23 mmole, 1.1 eq), tris(dibenzylideneacetone)dipalladium(0) (0.2 g, 0.22 mmole, 2% Pd) and potassium fluoride (4.4 g, 76 mmole, 3.3 eq) were suspended in anhydrous dioxane (30 ml). To the obtained suspension, a toluene solution of tri-t-butylphosphine (66%, 0.13 ml, 0.42 mmole, 1 eq) was added and the resultant mixture was stirred at 80° C. for 3 hours. The reaction mixture was filtered and washed with toluene (100 ml). The filtrate was washed with a saturated aqueous solution of sodium chloride (30 ml) and dried with magnesium sulfate. Then, the solvent was removed by distillation and a yellow solid was obtained. The obtained solid was washed with boiling ethanol (50 ml) and a yellow solid (5.2 g, 87%) was obtained. 1H-NMR (CDCl$_3$, TMS) δ: 7.4 to 7.6 (3H, m), 7.6 to 7.9 (4H, m), 7.98 (1H, dd, J=8 Hz, 2 Hz), 8.2 to 8.4 (3H, m), 8.50 (1H, d, J=2 Hz)

(2) Synthesis of 2-phenyl-9,10-bis(4-(2,2-diphenylvinyl)phenyl)-9,10-dihydroxy-9,10-dihydroanthracene Under an atmosphere of argon, 4-(2,2-diphenylvinyl) bromobenzene (5.0 g, 15 mmole, 2.6 eq) was dissolved into a mixed solvent composed of anhydrous toluene (25 ml) and anhydrous THF (25 ml) and the resultant solution was cooled at –40° C. in a dry ice/methanol bath. To the cooled solution, a hexane solution of n-butyllithium (1.60 mole/liter, 10 ml, 16 mmole, 1.1 eq) was added and the resultant mixture was stirred at –20° C. for 1 hour. To the obtained mixture, 2-phenylanthraquinone (1.6 g, 5.6 mmole) was added and the resultant mixture was stirred at –20° C. for 1 hour and at the room temperature for 7 hours and left standing for one night. To the obtained reaction mixture, a saturated aqueous solution of ammonium chloride (50 ml) was added and the reaction was deactivated. The formed organic layer was separated by filtration, washed with a saturated aqueous solution of sodium chloride (30 ml) and dried with magnesium sulfate. Then, the solvent was removed by distillation and a yellow oil was obtained. The obtained oil was purified by the column chromatography (silica gel/hexane+50% dichloromethane, dichloromethane and hexane+1% methanol, successively) and a white amorphous solid (2.3 g, 52%) was obtained.

$^1$H-NMR (CDCl$_3$, TMS) δ: 2.75 (1H, s), 2.78 (1H, s), 6.68 (8H, s), 6.83 (2H, s), 7.1 to 7.7 (31H, m), 7.90 (1H, d, J=2 Hz)

(3) Synthesis of 3-phenyl-9,10-bis(4-(2,2-diphenylvinyl)phenyl)-anthracene (Compound 34)

2-Phenyl-9,10-bis(4-(2,2-diphenylvinyl)phenyl)-9,10-dihydroxy-9,10-dihydroanthracene (2.3 g, 2.9 mmole) was dissolved into acetic acid (20 ml). To the resultant solution, potassium iodide (1.4 g, 8.4 mmole, 3 eq) and sodium phosphinate monohydrate (0.4 g, 3.8 mmole) were added and the obtained solution was stirred for 1 hours. The reaction mixture was filtered and washed with water, methanol and acetone and a light yellow solid (2.1 g, 95%) was obtained.

$^1$H-NMR (CDCl$_3$, TMS) δ: 7.14 (2H, s), 7.2 to 7.5 (39H, m), 7.87 (1H, s)

The solid obtained above (2.1 g) was purified by sublimation at 370° C. under 10$^{-6}$ Torr for 1 hour and a light yellow solid (0.9 g) was obtained.

FDMS: calc. for C$_{60}$H$_{42}$=762, found m/z=762 (M$^+$, 100)
λmax, 409, 388, 370 nm (PhMe)
Fmax, 453 nm (PhMe, λex=409 nm)
Eg=2.85 eV
Ip=5.70 eV (14 Y/eV, 100 nW)
Tg=114° C.

SYNTHESIS EXAMPLE 13

Compound 41

(1) Synthesis of 9-(4-bromophenyl)anthraquinone

Under an atmosphere of argon, 9-anthraceneboronic acid (11.8 g, 53 mmole), 4-iodobromobenzene (16.5 g, 58 mmole, 1.1 eq) and tetrakis-(triphenylphosphine)palladium (0) (1.0 g, 0.87 mmole, 1.5% Pd) were dissolved in toluene (160 ml). To the obtained solution, a 2 M aqueous solution of sodium carbonate (17 g, 0.16 mole, 3 eq/80 ml) was added and the resultant solution was heated under refluxing for 10 hours. The formed organic layer was separated, washed with a 5% aqueous solution of sodium hydroxide (100 ml) and a saturated aqueous solution of sodium chloride (50 ml) and dried with magnesium sulfate. Then, the solvent was removed by distillation and a light yellow solid was obtained. The obtained solid was purified by recrystallization from toluene (30 ml) and white plate crystals (10 g, 57%) were obtained.

$^1$H-NMR (CDCl$_3$, TMS) δ: 7.2 to 7.8 (10H, m), 8.0 to 8.1 (2H, m), 8.49 (1H, s)

(2) Synthesis of 9-bromo-10-(4-bromophenyl)anthracene 9-(4-Bromophenyl)anthracene (6.3 g, 19 mmole) was dissolved in anhydrous dimethylformamide (DMF) (100 ml). To the resultant solution, a solution (15 ml) of NBS (3.7 g, 21 mmole, 1.1 eq) in anhydrous DMF was added and the obtained mixture was stirred at the room temperature for 7 hours and left standing for one night. After the reaction mixture was diluted with water (30 ml), the formed solid was separated by filtration and washed with methanol and a yellow solid (6.0 g, 77%) was obtained.

$^1$H-NMR (CDCl$_3$, TMS) δ: 7.2 to 7.8 (10H, m), 8.60 (2H, d, J=9 Hz)

(3) Synthesis of 9-(4-(2,2-diphenylvinyl)phenyl)-10-(4-(4-(2,2-diphenylvinyl)phenyl)phenyl) (Compound 41)

Under an atmosphere of argon, 9-bromo-10-(4-bromophenyl)anthracene (3.0 g, 7.3 mmole), 4-(2,2-diphenylvinyl)phenylboronic acid (5.7 g, 19 mmole, 2.6 eq) and tetrakis(triphenylphosphine)palladium(0) (0.34 g, 0.29 mmole, 2% Pd) were suspended into toluene (60 ml). To the obtained suspension, a 2 M aqueous solution of sodium carbonate (6.0 g, 57 mmole, 3 eq/30 ml) was added and the resultant mixture was heated under refluxing for 10 hours. The reaction mixture was filtered and washed with toluene, water and methanol and a green solid (4.5 g) was obtained. The obtained solid was suspended in boiling toluene (50 ml), cooled while being left standing, filtered and washed with toluene and a light green solid (3.9 g, 70%) was obtained.

$^1$H-NMR (CDCl$_3$, TMS) δ: 7.0 to 7.5 (34H, m), 7.6 to 7.8 (8H, m)

The solid obtained above (3.9 g) was purified by sublimation at 380° C. under 10$^{-6}$ Torr for 2 hours and a light yellow solid (3.3 g) was obtained.

FDMS: calc. for C$_{60}$H$_{42}$=762, found m/z=762 (M$^+$, 100), 381 (M$^{2+}$, 7)

λmax, 397, 378, 357, 323 nm (PhMe)
Fmax, 442 nm (PhMe, λex=397 nm)
Eg=2.95 eV
Ip=5.62 eV (32 Y/eV, 100 nW)
Tg=120° C.

SYNTHESIS EXAMPLE 14

Compound 42

(1) Synthesis of 9-(3-(2,2-diphenylvinyl)phenyl)-10-(4-(3-(2,2-diphenylvinyl)phenyl)phenyl) (Compound 42)

Under an atmosphere of argon, 9-bromo-10-(4-bromophenyl)anthracene (3.0 g, 7.3 mmole), 4-(2,2-diphenylvinyl)phenylboronic acid (6.6 g, 22 mmole, 3 eq) and tetrakis(triphenylphosphine)palladium(0) (0.34 g, 0.29 mmole, 2% Pd) were suspended into toluene (60 ml). To the obtained suspension, a 2 M aqueous solution of sodium carbonate (7.0 g, 66 mmole, 3 eq/35 ml) was added and the resultant mixture was heated under refluxing for 10 hours. The reaction mixture was filtered and washed with toluene, water and methanol and a gray solid (1.4 g, the first crop, 25%) was obtained. From the filtrate, the organic layer was separated, washed with a saturated aqueous solution of sodium chloride and dried with magnesium sulfate. The solvent was removed by distillation and a deep brown oil was obtained. When the obtained oil was dissolved in dichloromethane, crystals were formed soon. The formed crystals were separated by filtration and washed with a mixed solvent composed of hexane and dichloromethane and a white solid (3.3 g, the second crop, 59%) was obtained. The obtained crude crystals (3.5 g) were suspended in boiling toluene (40 ml), cooled while being left standing, filtered and washed with toluene and a light yellow solid (2.4 g) was obtained.

$^1$H-NMR (CDCl$_3$, TMS) δ: 7.1 to 7.6 (32H, m) all-H

The solid obtained above (2.4 g) was purified by sublimation at 380° C. under 10$^{-6}$ Torr for 1 hour and a light yellow solid (1.9 g) was obtained.

FDMS: calc. for C$_{60}$H$_{42}$=762, found m/z=762 (M$^+$, 100), 508 (imp, 2), 381 (M$^{2+}$, 7)

λmax, 397, 377, 357 nm (PhMe)
Fmax, 423, 436 nm (PhMe, λex=397 nm)
Eg=3.00 eV
Ip=5.77 eV (17 Y/eV, 100 nW)
Tg=108° C.

SYNTHESIS EXAMPLE 15

Compound 43

(1) Synthesis of 9-(4-formylphenyl)anthracene

Under an atmosphere of argon, 9-bromoanthracene (3.9 g, 15 mmole), 4-formylphenylboronic acid (2.5 g, 17 mmole, 1.1 eq), potassium fluoride (3.2 g, 56 mmole, 3 eq) and tris(dibenzylideneacetone)dipalladium(0) (0.07 g, 76 mmole, 1% Pd) were suspended in anhydrous THF (25 ml). To the obtained suspension, a toluene solution of tri-t-butylphosphine (66%, 0.06 ml, 0.2 mmole, 1.3 eq to Pd) was added and the resultant mixture was heated under refluxing for 10 hours. To the reaction mixture, water (50 ml) and toluene (150 ml) were added. The formed organic layer was separated, washed with a saturated aqueous solution of sodium chloride (50 ml) and dried with magnesium sulfate. Then, the solvent was removed by distillation and a light yellow solid was obtained. The obtained solid was purified by the column chromatography (silica gel/hexane+50% dichloromethane) and a light yellow solid (3.3 g, 78%) were obtained.

$^1$H-NMR (CDCl$_3$, TMS) δ: 7.3 to 7.7 (8H, m), 8.0 to 8.1 (2H, m), 8.10 (2H, d, J=8 Hz,), 8.52 (1H, s), 10.18 (1H, s)

(2) Synthesis of 9-bromo-10-(4-formylphenyl)anthracene 9-(4-Formylphenyl)anthracene (3.3 g, 12 mmole) was suspended in anhydrous DMF (40 ml). To the resultant suspension, a solution (8 ml) of NBS (2.3 g, 13 mmole, 1.1 eq) in anhydrous DMF was added and the obtained mixture was stirred at the room temperature for 10 hours and left standing for one night. After the reaction mixture was diluted with water (50 ml), the solid was separated by filtration and washed with methanol and a yellow solid (3.9 g, 90%) was obtained.

$^1$H-NMR (CDCl$_3$, TMS) δ: 7.3 to 7.7 (8H, m), 8.10 (2H, d, J=8 Hz), 8.62 (2H, dd, J=8 Hz, 2 Hz), 10.19 (1H, s)

(3) Synthesis of 9-bromo-10-(4-(2-phenylvinyl)phenyl)anthracene

Under an atmosphere of argon, 9-bromo-10-(4-formylphenyl)anthracene (3.9 g, 11 mmole) and diethyl benzylphosphonate (3 g, 13 mmole, 1.2 eq) were suspended into DMSO (25 ml). To the resultant suspension, potassium t-butoxide (1.6 g, 14 mmole, 1.1 eq) was added and the obtained mixture was stirred at the room temperature for 10 hours and left standing for one night. The reaction mixture was diluted with water (50 ml) and subjected to extraction with toluene (300 ml). The organic layer was washed with water (50 ml) and a saturated aqueous solution of sodium chloride (50 ml) and dried with magnesium sulfate. Then, the solvent was removed by distillation and a yellow solid was obtained. The obtained solid was purified by recrystallization from toluene (40 ml) and yellow needle crystals (4.1 g, 86%) were obtained.

$^1$H-NMR (CDCl$_3$, TMS) δ: 7.2 to 7.8 (17H, m), 8.60 (2H, d, J=8 Hz)

(4) Synthesis of 9-(4-(2,2-diphenylvinyl)phenyl)-10-(4-(2-phenylvinyl)phenyl)anthracene (Compound 43)

Under an atmosphere of argon, 9-bromo-10-(4-(2-phenylvinyl)phenyl)anthracene (3.1 g, 7.1 mmole), 4-(2,2-diphenylvinyl)phenylboronic acid (2.4 g, 8.0 mmole, 1.1 eq) and tetrakis(triphenylphosphine)palladium(0) (0.16 g, 0.14 mmole, 2% Pd) were suspended into toluene (25 ml). To the obtained suspension, a 2 M aqueous solution of sodium carbonate (2.5 g, 24 mmole, 3 eq/12 ml) was added and the resultant mixture was heated under refluxing for 10 hours. The reaction mixture was filtered and washed with water and methanol and a yellow solid was obtained. The obtained solid was suspended in boiling toluene (50 ml), cooled while being left standing, filtered and washed with toluene and a light yellow solid (3.8 g, 88%) was obtained.

$^1$H-NMR (CDCl$_3$, TMS) δ: 7.14 (2H, s), 7.3 to 7.8 (32H, m)

The solid obtained above (3.8 g) was purified by sublimation at 340° C. under 10$^{-6}$ Torr for 1 hour and a light yellow solid (2.9 g) was obtained.

FDMS: calc. for C$_{48}$H$_{34}$=610, found m/z=610 (M$^+$, 100), 305 (M$^{2+}$, 5)

λmax, 398, 379, 360, 313, 304 nm (PhMe)

Fmax, 445 nm (PhMe, λex=397 nm)

Eg=2.94 eV

Ip=5.68 eV (12 Y/eV, 100 nW)

EXAMPLE 1

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of N,N'-bis(N,N'-diphenyl-4-aminophenyl)-N,N'-diphenyl-4,4'-diamino-1,1'-biphenyl (referred to as TPD232, hereinafter) having a thickness of 60 nm was formed so that the formed film covered the transparent electrode. The formed film of TPD232 worked as the first hole injecting layer (the hole transporting layer). Then, on the formed film of TPD232, a film of 4,4'-bis[N-(1-naphthyl)-N-phenylamino]-biphenyl (referred to as NPD, hereinafter) having a thickness of 20 nm was formed. The formed film of NPD worked as the second hole injecting layer (the hole transporting layer). On the formed film of NPD, Compound (15) was vacuum vapor deposited so that a film having a thickness of 40 nm was formed. The film of compound (15) worked as the light emitting layer. On the film formed above, a film of tris(8-quinolinol)aluminum (referred to as Alq, hereinafter) having a thickness of 20 nm was formed. The film of Alq worked as the electron injecting layer. Thereafter, Li (the source of lithium: manufactured by SAES GETTERS Company) and Alq were binary vapor deposited and an Alq:Li film was formed as the electron injecting layer (the cathode). On the formed Alq:Li film, metallic aluminum was vapor deposited to form a metal cathode and an organic EL device was prepared. When a direct current voltage of 6 V was applied to the organic EL device prepared above, blue light was emitted at a luminance of 80 cd/m$^2$, a maximum luminance of 23,000 cd/m$^2$ and an efficiency of light emission of 2.0 cd/A.

The spectrum of the light emitted from this organic EL device is shown in FIG. 1. As shown in FIG. 1, the light emitted from this organic EL device had the peak wavelength at 450 nm and exhibited excellent purity of color.

Compound 15 had a glass transition temperature of 118° C. and exhibited excellent heat resistance. When the obtained organic EL device was kept at a high temperature (85° C., 500 hours), no change was found in the properties and the excellent heat resistance was confirmed.

When the device was driven under a constant current at an initial luminance of 80 cd/m$^2$, the half-life was as long as 13,000 hours.

EXAMPLES 2 TO 14

Organic EL devices were prepared in accordance with the same procedures as those conducted in Example 1 except that the compounds shown in Table 1 were used in place of Compound (15). A direct current voltage of 6 V was applied to the prepared organic EL devices. The luminance of the emitted light and the efficiency of light emission were measured and the color of the emitted light was observed. The results are shown in Table 1.

TABLE 1

| | Compound | Luminance of emitted light (cd/m$^2$) | Efficiency of light emission (cd/A) | Color of emitted light |
|---|---|---|---|---|
| Example 2 | (1) | 120 | 3.2 | blue |
| Example 3 | (2) | 113 | 2.7 | blue |
| Example 4 | (3) | 90 | 3.7 | blue |
| Example 5 | (13) | 130 | 2.2 | blue |
| Example 6 | (14) | 113 | 2.7 | blue |
| Example 7 | (17) | 90 | 4.2 | blue |
| Example 8 | (20) | 150 | 2.8 | blue |
| Example 9 | (22) | 180 | 4.7 | blue |
| Example 10 | (25) | 80 | 2.8 | blue |
| Example 11 | (26) | 75 | 2.6 | blue |
| Example 12 | (33) | 230 | 3.6 | blue |
| Example 13 | (34) | 280 | 4.3 | blue |
| Example 14 | (41) | 250 | 4.2 | blue |

EXAMPLES 15 TO 25 AND COMPARATIVE EXAMPLES 1 AND 2

The glass transition temperatures of the novel compounds of the present invention shown in Table 2 and Compound C1 (Comparative Example 1):

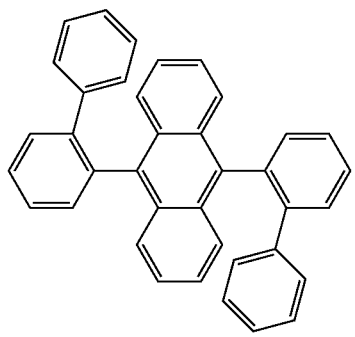

(C1)

and Compound C2 (Comparative Example 2):

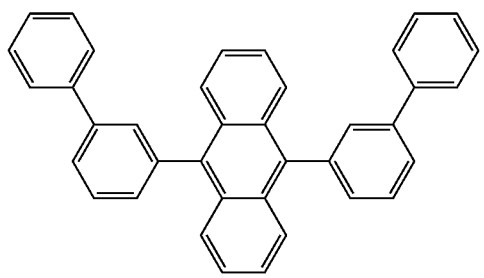

(C2)

were obtained by the measurement of DSC. The results are shown in Table 2.

TABLE 2

| | Compound | Glass transition temperature (° C.) |
|---|---|---|
| Example 15 | (14) | 102 |
| Example 16 | (15) | 118 |

TABLE 2-continued

| | Compound | Glass transition temperature (° C.) |
|---|---|---|
| Example 17 | (17) | 163 |
| Example 18 | (18) | 106 |
| Example 19 | (22) | 110 |
| Example 20 | (24) | 113 |
| Example 21 | (25) | 130 |
| Example 22 | (26) | 135 |
| Example 23 | (33) | 105 |
| Example 24 | (34) | 110 |
| Example 25 | (41) | 120 |
| Comparative Example 1 | (C1) | 75 |
| Comparative Example 2 | (C2) | 97 |

As shown in Table 2, the compounds of Comparative Examples had glass transition temperatures lower than 100° C. and exhibited poor heat resistance. In contrast, the compounds of Examples had glass transition temperatures higher than 100° C. and exhibited excellent heat resistance.

EXAMPLE 26

An organic EL device was prepared in accordance with the same procedures as those conducted in Example 1 except that, in place of Compound (15), Compound (15) and the following compound PAVB:

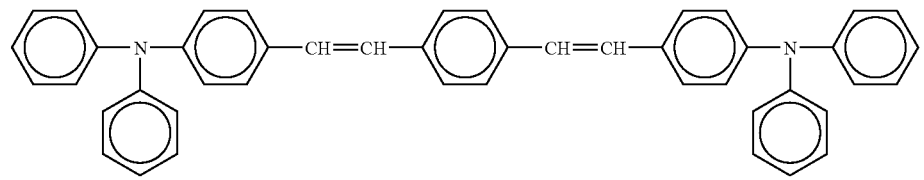

which worked as the fluorescent dopant were binary vapor deposited at a relative rate of vapor deposition of 40:1 and a film was formed. Under the application of a direct current voltage of 5.5 V to the prepared organic EL devices, the luminance of emitted light, the efficiency of light emission and the maximum luminance of emitted light were measured and the color of the emitted light was observed. The results are shown in Table 3.

EXAMPLE 27

An organic EL device was prepared in accordance with the same procedures as those conducted in Example 1 except that, in place of Compound (15), Compound (17) and PAVB shown above were binary vapor deposited at a relative rate of vapor deposition of 40:1 and a film was formed. Under the application of a direct current voltage of 5.5 V to the prepared organic EL devices, the luminance of emitted light, the efficiency of light emission and the maximum luminance of emitted light were measured and the color of the emitted light was observed. The results are shown in Table 3.

EXAMPLE 28

An organic EL device was prepared in accordance with the same procedures as those conducted in Example 1 except that, in place of Compound (15), Compound (18) and PAVB shown above were binary vapor deposited at a relative rate of vapor deposition of 40:1 and a film was formed. Under the application of a direct current voltage of 5.5 V to the prepared organic EL devices, the luminance of emitted light, the efficiency of light emission and the maximum luminance of emitted light were measured and the color of the emitted light was observed. The results are shown in Table 3.

TABLE 3

|  | Compound | Luminance of emitted light (cd/m$^2$) | Efficiency of light emission (cd/A) | Maximum luminance of emitted light (cd/m$^2$) | Color of emitted light |
|---|---|---|---|---|---|
| Example 26 | (15) and PAVB | 222 | 7.14 | 85,000 | greenish blue |
| Example 27 | (17) and PAVB | 135 | 7.58 | 75,000 | greenish blue |
| Example 28 | (18) and PAVB | 145 | 9.67 | 95,000 | greenish blue |

As shown in Table 3, the efficiency was improved by adding the fluorescent dopant to the novel compound of the present invention.

COMPARATIVE EXAMPLE 3

An organic EL device was prepared in accordance with the same procedures as those conducted in Example 1 except that, in place of Compound (15), the following Compound (C3):

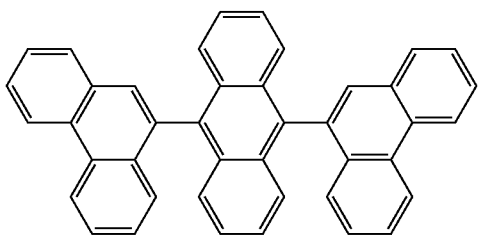

was vapor deposited and a film was formed. When a direct current voltage of 6.5 V was applied to the organic EL device prepared above, bluish green light was emitted at a luminance of 92 cd/m$^2$ and an efficiency of light emission of 1.22 cd/A. The efficiency was low and the device could not be used for a practical application.

EXAMPLE 29

An organic EL device was prepared in accordance with the same procedures as those conducted in Example 1 except that Compound (25) was used in place of Compound (15). When the device prepared above was driven under a constant current at an initial luminance of 500 cd/m$^2$, the half-life was as long as 840 hours which corresponded to about 6,000 hours at an initial luminance of 100 cd/m$^2$. When the organic EL device was kept at a high temperature (85° C., 500 hours), no change was found in the properties and the heat resistance was excellent. The light emission on the light emitting surface was uniform and showed no defects. The device exhibited an efficiency of light emission of 2.8 cd/A and blue light of a high purity having color coordinates of (0.16, 0.08) was emitted.

EXAMPLE 30

An organic EL device was prepared in accordance with the same procedures as those conducted in Example 1 except that Compound (33) was used in place of Compound (15). When the device prepared above was driven under a constant current at an initial luminance of 500 cd/m$^2$, the half-life was as long as 1,100 hours which corresponded to about 8,000 hours at an initial luminance of 100 cd/m$^2$. When the organic EL device was kept at a high temperature (85° C., 500 hours), no change was found in the properties and the heat resistance was excellent. The light emission on the light emitting surface was uniform and showed no defects. The device exhibited an excellent efficiency of light emission of 3.6 cd/A.

EXAMPLE 31

An organic EL device was prepared in accordance with the same procedures as those conducted in Example 1 except that Compound (41) was used in place of Compound (15). When the device prepared above was driven under a constant current at an initial luminance of 500 cd/m$^2$, the half-life was as long as 1,200 hours which corresponded to about 9,500 hours at an initial luminance of 100 cd/m$^2$. When the organic EL device was kept at a high temperature (85° C., 500 hours), no change was found in the properties and the heat resistance was excellent. The light emission on the light emitting surface was uniform and showed no defects. Blue light of a high purity having color coordinates of (0.15, 0.13) was emitted and the device exhibited an excellent efficiency of light emission of 4.2 cd/A.

COMPARATIVE EXAMPLE 4

An organic EL device was prepared in accordance with the same procedures as those conducted in Example 1 except that, in place of Compound (15), the following Compound (C4):

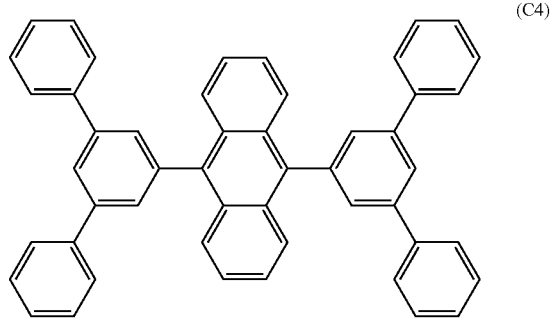

was vapor deposited and a film was formed. When the device prepared above was driven under a constant current at an initial luminance of 500 cd/m², the half-life was as extremely short as 25 hours and the device could not be used for practical applications. The efficiency of light emission was as low as 1.7 cd/A.

COMPARATIVE EXAMPLE 5

An organic EL device was prepared in accordance with the same procedures as those conducted in Example 1 except that, in place of Compound (15), the following Compound (C5):

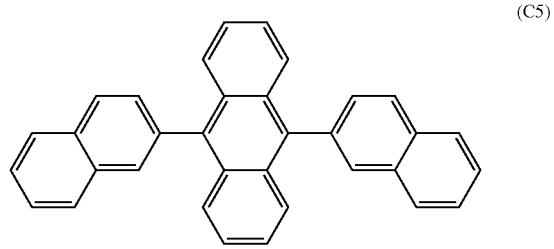

(C5)

was vapor deposited and a film was formed. When the device prepared above was driven under a constant current at an initial luminance of 500 cd/m², the half-life was as short as 420 hours and the device could not be used for practical applications. The efficiency of light emission was as low as 2.1 cd/A.

COMPARATIVE EXAMPLE 6

An organic EL device was prepared in accordance with the same procedures as those conducted in Example 1 except that, in place of Compound (15), the following Compound (C6):

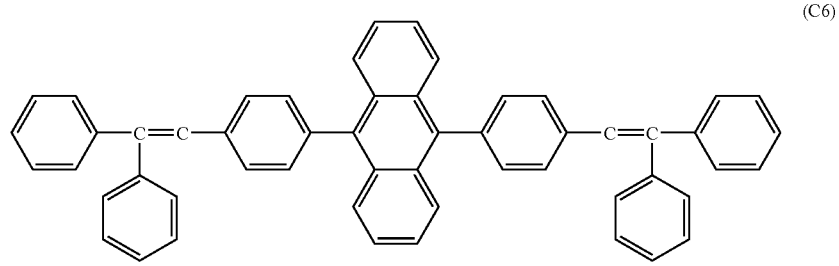

(C6)

was vapor deposited and a film was formed. When this device prepared above was kept at a high temperature (85° C., 500 hours), defects were formed at portions of the light emitting surface and the portions of the defects showed change in the color although the half-life was as long as 1,000 hours when the device was driven under a constant current at an initial luminance of 500 cd/m².

As described above, the devices prepared by using the compounds of the present invention could emit blue light at an efficiency of light emission of 2 cd/A or higher and were more excellent than the devices of Comparative Examples.

The devices prepared by using the compounds of the present invention also had long lives, exhibited excellent heat resistance and could maintain uniform light emission after being kept at a high temperature.

INDUSTRIAL APPLICABILITY

As described above in detail, the organic electroluminescence device of the present invention which utilizes any of the above novel compounds represented by general formulae [1], [1'] and [2] to [5] exhibits excellent efficiency of light emission and heat resistance, has a long life and emits bluish light having excellent purity of color.

Therefore, the organic electroluminescence device of the present invention is useful as a light source such as a planar light emitting member of wall televisions and a back light of displays.

What is claimed is:

1. A compound selected from the group consisting of

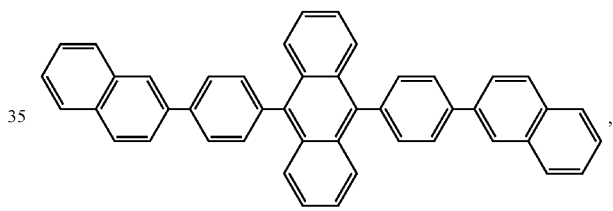

,

-continued
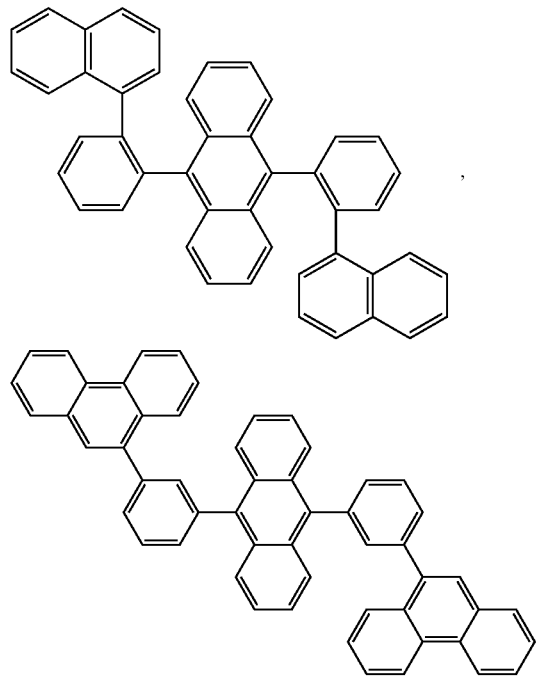
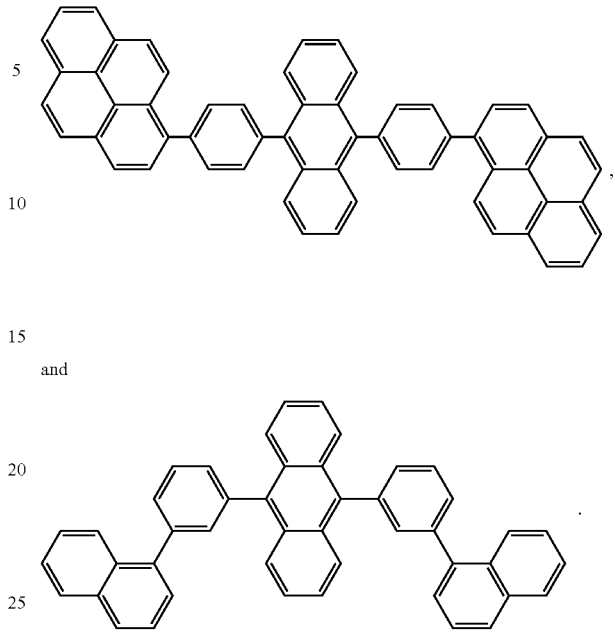
and
* * * * *